United States Patent
Lee et al.

(10) Patent No.: US 11,756,241 B2
(45) Date of Patent: *Sep. 12, 2023

(54) POSITRON EMISSION TOMOGRAPHY SYSTEM AND IMAGE RECONSTRUCTION METHOD USING THE SAME

(71) Applicant: Seoul National University R&DB Foundation, Seoul (KR)

(72) Inventors: Jae Sung Lee, Seoul (KR); Donghwi Hwang, Seoul (KR); Kyeong Yun Kim, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 282 days.

This patent is subject to a terminal disclaimer.

(21) Appl. No.: 17/169,687

(22) Filed: Feb. 8, 2021

(65) Prior Publication Data

US 2021/0166444 A1    Jun. 3, 2021

Related U.S. Application Data

(63) Continuation-in-part of application No. 16/282,513, filed on Feb. 22, 2019, now Pat. No. 10,943,349.

(30) Foreign Application Priority Data

Feb. 23, 2018   (KR) .................. 10-2018-0021902

(51) Int. Cl.
*G06T 11/00*    (2006.01)
*G06T 3/40*    (2006.01)
(Continued)

(52) U.S. Cl.
CPC ............ *G06T 11/005* (2013.01); *A61B 6/037* (2013.01); *A61B 6/5258* (2013.01);
(Continued)

(58) Field of Classification Search
CPC ..... G06T 7/0016; G06T 11/005; G16H 30/40; A61B 5/7221; A61B 6/037; A61B 5/7267; G01T 1/2985; G06K 9/6232
See application file for complete search history.

(56) References Cited

U.S. PATENT DOCUMENTS

| 2010/0049032 A1* | 2/2010 | Steinke ..................... G06T 7/33 |
| | | 600/416 |
| 2014/0056500 A1 | 2/2014 | Bal et al. |

(Continued)

FOREIGN PATENT DOCUMENTS

| KR | 10-1331504 | 11/2013 |
| KR | 10-2018-0029476 | 3/2018 |

OTHER PUBLICATIONS

Ahmadreza Rezaei et al., "Simultaneous Reconstruction of Activity and Attenuation in Time-of-Flight PET", IEEE Transactions On Medical Imaging, vol. 31, No. 12, Dec. 2012.

(Continued)

*Primary Examiner* — Md K Talukder
(74) *Attorney, Agent, or Firm* — LEX IP MEISTER, PLLC

(57) ABSTRACT

Disclosed are a positron emission tomography system and an image reconstructing method using the same and the positron emission tomography system includes: a collection unit collecting a positron emission tomography sinogram (PET sinogram); an image generation unit applying the positron emission tomography sinogram to an MLAA with TOF and generating a first emission image and a first attenuation image and a NAC image reconstructed without attenuation correction; and a control unit selecting at least one of the first emission image, the first attenuation image and the NAC image generated by the image generation unit as an input image and generating and providing a final (Continued)

attenuation image by applying the input image to the learned deep learning algorithm.

13 Claims, 22 Drawing Sheets

(51) Int. Cl.
  *A61B 6/03* (2006.01)
  *A61B 6/00* (2006.01)
  *G01T 1/29* (2006.01)

(52) U.S. Cl.
  CPC .............. *G01T 1/2985* (2013.01); *G06T 3/40* (2013.01); *G06T 2210/41* (2013.01)

(56) References Cited

U.S. PATENT DOCUMENTS

| | | | |
|---|---|---|---|
| 2018/0197317 | A1 | 7/2018 | Cheng et al. |
| 2018/0374205 | A1* | 12/2018 | Zhu .......................... G06T 5/007 |
| 2019/0266728 | A1* | 8/2019 | Lee .......................... A61B 6/037 |
| 2019/0378293 | A1* | 12/2019 | Mwikirize ................ G06T 5/20 |
| 2020/0211236 | A1* | 7/2020 | Zhang ................... G06T 11/008 |

OTHER PUBLICATIONS

Donghwi Hwang et al., "Improving the Accuracy of Simultaneously Reconstructed Activity and Attenuation Maps Using Deep Learning", The Journal of Nuclear Medicine, vol. 59, No. 10, pp. 1624-1629, Oct. 1, 2018. (First published Feb. 15, 2018, doi: 10.2967/jnumed.117.202317).

Sarah C. Cade et al., "Use of measured scatter data for the attenuation correction of single photon emission tomography without transmission scanning", Medical Physics, vol. 40, No. 8, Aug. 2013.

Xiao Han, "MR-based synthetic CT generation using a deep convolutional neural network method", Medical Physics, vol. 44, No. 4, Apr. 2017.

Abolfazl Mehranian et al., "Joint Estimation of Activity and Attenuation in Whole-Body TOF PET/MRI Using Constrained Gaussian Mixture Models", IEEE Transactions On Medical Imaging, vol. 34, No. 9, Sep. 2015.

Michel Defrise et al., Transmission-less attenuation correction in time-of-flight PET: analysis of a discrete iterative algorithm, Physics in Medicine and Biology, vol. 59, 2014, pp. 1073-1095.

Ian J. Goodfellow et al., "Generative Adversarial Nets", Generative Adversarial Network, NIPS, 2014.

Karen Simonyan et al., "Very Deep Convolutional Networks for Large-Scale Image Recognition", ICLR, VGGNet, 2015.

Kaiming He et al., "Deep Residual Learning for Image Recognition", CVPR, ResNet, 2016.

Kai Zhang et al., "Beyond a Gaussian Denoiser: Residual Learning of Deep CNN for Image Denoising", DnCNN, 2016, IEEE Transactions On Image Processing, vol. 26, No. 7, Jul. 2017.

Gao Huang et al., "Densely Connected Convolutional Networks", CVPR, DenseNet, 2017.

Olaf Ronneberger et al., "U-Net: Convolutional Networks for Biomedical Image Segmentation", MICCAI, pp. 234-241, 2015.

Andrew P. Leynes et al., "Zero-Echo-Time and Dixon Deep Pseudo-CT (ZeDD CT): Direct Generation of Pseudo-CT Images for Pelvic PET/MRI Attenuation Correction Using Deep Convolutional Neural Networks with Multiparametric MRI", The Journal of Nuclear Medicine, vol. 59, No. 5, May 2018.

Donghwi Hwang et al., "Generation of PET attenuation map for whole-body time-of-flight F-FDG PET/MRI using a deep neural network trained with simultaneously reconstructed activity and attenuation maps", The Journal of Nuclear Medicine, Jan. 25, 2019. (First published Jan. 25, 2019, doi: 10.2967/junmed.118.219493).

* cited by examiner

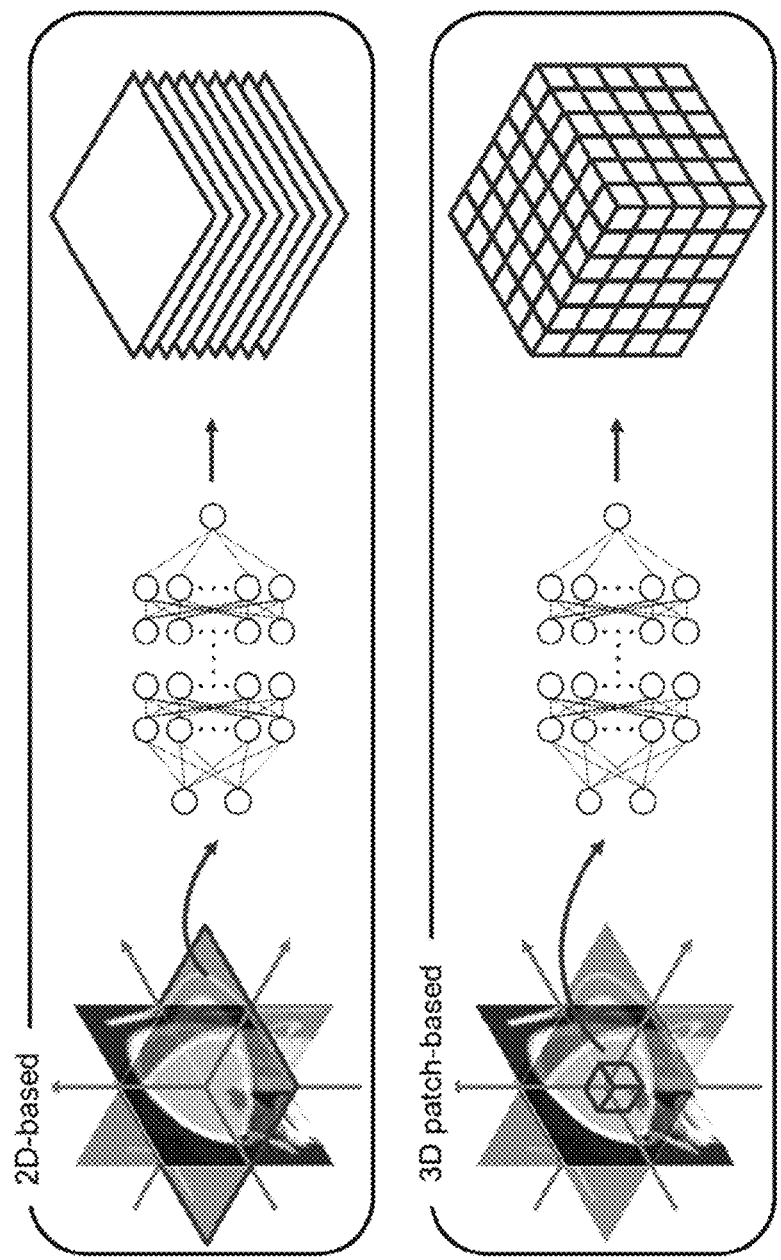

POSITRON EMISSION TOMOGRAPHY SYSTEM AND IMAGE RECONSTRUCTION METHOD USING THE SAME

CROSS-REFERENCE TO RELATED APPLICATION

This application is a Continuation in part application of U.S. patent application Ser. No. 16/282,513, which was filed on Feb. 22, 2019, which claims priority to and the benefit of Korean Patent Application No. 10-2018-0021902 filed in the Korean Intellectual Property Office on Feb. 23, 2018, the entire contents of which are incorporated herein by reference.

BACKGROUND OF THE INVENTION

(a) Field of the Invention

The present invention relates to a positron emission tomography system and an image reconstruction method using the same.

(b) Description of the Related Art

Positron emission tomography (PET) is a nuclear medicine testing method that can show physiological/chemical and functional images of a body in three dimensions using radiopharmaceuticals emitting positron.

At present, the positron emission tomography (CT) is widely used to diagnose various cancers and is evaluated as a useful test for differential diagnosis of cancer, stage setting, recurrence evaluation, and judgment of treatment effect.

In general, a positron emission tomography (PET) device needs to perform a process of correcting and reconstructing an image in order to check at which portion of a body the radiopharmaceuticals are collected from raw data and how much the radiopharmaceuticals are collected by providing the raw data by detecting two disappearing radiations (gamma rays) emitted from the positron.

In recent years, a positron emission tomography image is reconstructed by using anatomical information obtained from additional scan of computed tomography (CT) that obtains images by using an X-ray or magnetic resonance imaging (MRI) that obtains images by transferring high-frequency waves in a magnetic field.

FIG. 1A is an exemplary diagram illustrating a process of reconstructing a positron emission tomography image in the related art.

As illustrated in FIG. 1A, in a process of reconstructing the positron emission tomography image to an attenuated corrected emission image ($\lambda$-CT) through a reconstruction algorithm (ordered subset expectation maximization, OSEM), an attenuation image ($\mu$-CT) obtained through computed tomography of an X-ray is used.

Thus, reconstructing the image using the attenuation image obtained by the additional scan can correct the image more accurately and image quality is excellent, but an amount of a radiation received by a patient through the additional scan increases.

Therefore, in order to reconstruct the image with the positron emission tomography only, a simultaneous reconstruction algorithm (Maximum Likelihood reconstruction of Attenuation and Activity with Time-Of-Flight, MLAA with TOF) which can simultaneously obtain an attenuation image ($\mu$-MLAA) and an emission image ($\lambda$-MLAA) has been studied.

FIG. 1B is an exemplary diagram illustrating a process of generating an attenuation image and an emission image by using the MLAA with TOF in the related art in a positron emission tomography image.

As illustrated in FIG. 1B, the attenuation image ($\mu$-MLAA) and the emission image ($\lambda$-MLAA) can be obtained at the same time by using the MLAA with TOF without additional scan, but has a large error in the entire image from the attenuation image ($\mu$-CT) obtained through the additional scan in the related art.

In particular, since crosstalk artifact occurs in which a region where activity is high in the emission image appears in the attenuation image and distortion thus occurs, there are many difficulties in using the attenuation image and the emission image obtained by using the MLAA with TOF.

Therefore, there is a need for a technique capable of simultaneously obtaining a high-quality attenuation image and a high-quality emission image by the positron emission tomography only without shot of separate magnetic resonance imaging (MRI) or computed tomography (CT) for obtaining the attenuation image.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention has been made in an effort to obtain a high-quality attenuation image and a high-quality emission image only by a positron emission tomography image by using a deep learning algorithm.

Exemplary embodiments according to the present invention can be used to achieve other objects not specifically mentioned other than the objects.

An exemplary embodiment of the present invention provides a positron emission tomography system including: a collection unit collecting a positron emission tomography sinogram (PET sinogram); a generation unit applying an MLAA with TOF to the positron emission tomography sinogram and generating a first emission image and a first attenuation image, and a NAC image reconstructed without attenuation correction; and a control unit selecting at least one of the first emission image, the first attenuation image and the NAC image generated by the generation unit as an input image and generating and providing a final attenuation image by applying the learned deep learning algorithm to the input image.

The positron emission tomography system may further include a learning unit collecting an attenuation image obtained through additional scanning based on the positron emission tomography sinogram and learning a deep learning algorithm by using at least one of the first emission image, the first attenuation image and the NAC image generated from the positron emission tomography sinogram and the obtained attenuation image.

The learning unit may include an image generation unit generating a second attenuation image from the first attenuation image through the deep learning algorithm, an error calculation unit calculating an error between the second attenuation image and the obtained attenuation image, and a weight adjustment unit performing repeated learning by readjusting weights of a plurality of filters included in the deep learning algorithm so as to generate a final attenuation image in which the error value becomes a value equal to or less than a threshold value.

The image generation unit may generate a plurality of feature maps from the input image by using the filter of the deep learning algorithm and generate a sample downsized from the generated feature map at a predetermined ratio, and repeat a process of generating the plurality of feature maps in the downsized sample by using the filter until a size of the sample reaches a predetermined reference size, and upsize the sample at a predetermined ratio when the size of the sample reaches the predetermined reference size and generate the second attenuation image when the size of the upsized sample coincides with an initial size by repeating a process of generating the plurality of feature maps in the upsized sample by using the filter.

The image generation unit may upsize the sample and collect feature maps having the same size as that of the upsized sample and combine the collected feature maps and the sample at the time of generating the plurality of feature maps and generate the plurality of feature maps from the combined sample.

The control unit may select the first attenuation image generated by the image generation unit as an input image or select the first attenuation image, the first emission image and the NAC image as the input image to generate a final attenuation image through the learned deep learning algorithm.

The control unit may select some voxel data groups from the first attenuation image, the first emission image and the NAC image and apply the learned deep learning algorithm to the entire first attenuation image, first emission image and the NAC image by repeating a process of applying the learned deep learning algorithm to the selected voxel data groups to generate the final attenuation image in a 3D type.

The control unit may generate and provide a final emission image obtained by correcting the final attenuation image by using the first emission image and the final attenuation image.

Another exemplary embodiment of the present invention provides a method for reconstructing an image in a positron emission tomography system, including: collecting a positron emission tomography sinogram (PET sinogram); applying an MLAA with TOF to the positron emission tomography sinogram and generating a first emission image and a first attenuation image, and a NAC image reconstructed without attenuation correction; selecting the generated first attenuation image as an input image; generating and providing a final attenuation image, the first attenuation image and NAC image by applying the learned deep learning algorithm to the input image; and generating and providing a final emission image corrected by using the first emission image and the final attenuation image.

Yet another exemplary embodiment of the present invention provides a method for reconstructing an image in a positron emission tomography system, including: collecting a first emission image and a first attenuation image generated by an MLAA with TOF with a positron emission tomography sinogram (PET sinogram), and a NAC image reconstructed without attenuation correction; selecting at least one of the generated first attenuation image the first attenuation image and NAC image as an input image; generating and providing a final attenuation image by applying the learned deep learning algorithm to the input image; and generating and providing a final emission image corrected by using the first emission image and the final attenuation image.

According to an exemplary embodiment of the present invention, it is possible to obtain an attenuation image only by a positron emission tomography image without additional CT or MRI imaging, thereby minimizing a radiation amount received by a patient.

According to an exemplary embodiment of the present invention, a high-quality attenuation image can be obtained through a simultaneous reconstruction technique, thereby reducing cost and time required for reconstructing a positron emission tomography image.

According to an exemplary embodiment of the present invention, it is possible to provide a high-quality attenuation image by solving a quantitative error due to noise and crosstalk artifacts of an image, which occur due to the simultaneous reconstruction technique.

BRIEF DESCRIPTION OF THE DRAWINGS

FIGS. 6A, 6B, and 6C are exemplary diagrams for describing an input image of the deep learning algorithm according to an exemplary embodiment of the present invention.

DETAILED DESCRIPTION OF THE EMBODIMENTS

Figure 1A:
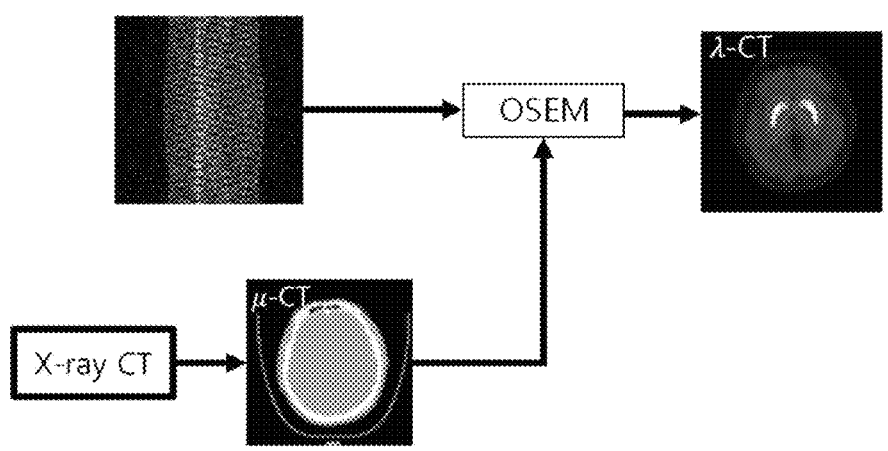
FIG. 1A is an exemplary diagram illustrating a process of reconstructing a positron emission tomography image in the related art.
Figure 1B:
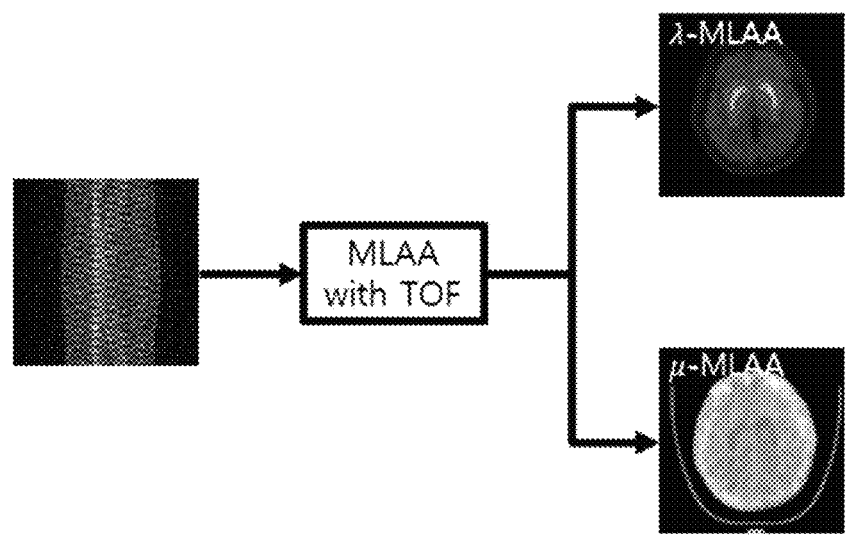
FIG. 1B is an exemplary diagram illustrating a process of generating an attenuation image and an emission image by using an MLAA with TOF in the related art in the positron emission tomography image.

An exemplary embodiment of the present invention will be described more fully hereinafter with reference to the accompanying drawings so as to be easily implemented by those skilled in the art. As those skilled in the art would realize, the described embodiments may be modified in various different ways, all without departing from the spirit or scope of the present invention. Parts not associated with description are omitted for clearly describing the present invention and like reference numerals designate like elements throughout the specification. Further, a detailed description of the related art which is widely known will be omitted.

Throughout the specification, unless explicitly described to the contrary, the word "comprise" and variations such as "comprises" or "comprising", will be understood to imply the inclusion of stated elements but not the exclusion of any other elements.

Figure 2:
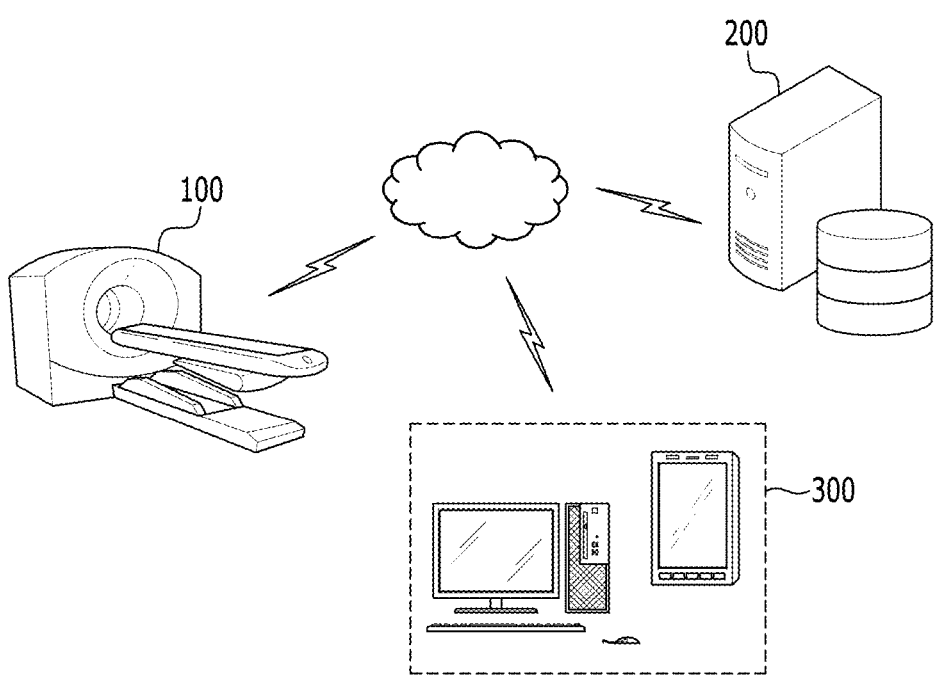
FIG. 2 is an exemplary diagram illustrating a communication network including a positron emission tomography system according to an exemplary embodiment of the present invention.

FIG. 2 is an exemplary diagram illustrating a communication network including a positron emission tomography system according to an exemplary embodiment of the present invention.

As illustrated in FIG. 2, a positron emission tomography device 100, a positron emission tomography system 200, and a user terminal 300 are connected to each other through a network to transmit/receive data.

Here, the network may include all types of communication networks that transfer data, which include a wired communication network, a local or remote wireless communication network, a network in which the wired communication network and the local or remote wireless communication network are mixed, and the like.

First, the positron emission tomography device 100 as a positron tomography (PET) scanner may detect two annihilation radiations which are formed in a cylindrical shape and simultaneously emitted.

In this case, the positron emission tomography device 100 is configured solely, not a type combined with a computed tomography (CT) or magnetic resonance imaging (MRI).

The positron emission tomography system 200 then connects directly to the positron emission tomography device 100 or collects a positron emission tomography (PET) sinogram through a storage device (not illustrated).

The positron emission tomography system 200 generates a first emission image and a first attenuation image in the positron emission tomography sinogram collected through an MLAA with TOF. In addition, the positron emission tomography system 200 applies the first attenuation image to a learned deep running algorithm to provide a final attenuation image.

The learned deep learning algorithm represents an artificial neural network that generates a final attenuation image having an error value of a threshold value or less from an attenuation image generated from another imaging device.

In this case, the positron emission tomography system 200 may construct the learned deep learning algorithm by repeatedly learning the deep learning algorithm by using the first attenuation image and the attenuation image generated from another imaging device in order to generate the final attenuation image.

Meanwhile, in FIG. 2, the positron emission tomography device 100 and the positron emission tomography system 200 are illustrated as separate devices, but the positron emission tomography system 200 may be later mounted on the positron emission tomography device 100 by a manager.

Next, the user terminal 300 refers to a medical device manager or a terminal of a medical staff who analyzes a positron emission tomography image and for example, the user terminal 300 is a personal computer, a handheld computer, a personal digital assistant, a cellular phone, a smart device, a tablet, or the like.

The user terminal 300 may be linked with the positron emission tomography 100 or the positron emission tomography system 200 to display or store or manage the positron emission tomography sinogram and the final attenuation image.

Hereinafter, a positron emission tomography system 200 for reconstructing the positron emission tomography image through the deep learning algorithm learned will be described in detail with reference to FIGS. 3 and 4.

Figure 3:
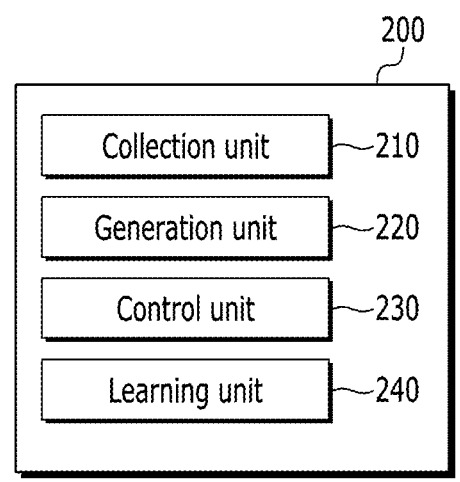
FIG. 3 is a configuration diagram illustrating the positron emission tomography system according to an exemplary embodiment of the present invention.
Figure 4:
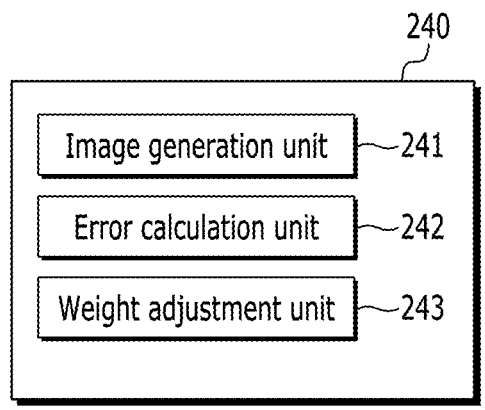
FIG. 4 is a configuration diagram of a learning unit according to an exemplary embodiment of the present invention.

FIG. 3 is a configuration diagram illustrating the positron emission tomography system according to an exemplary embodiment of the present invention and FIG. 4 is a configuration diagram of a learning unit according to an exemplary embodiment of the present invention.

As illustrated in FIG. 3, the positron emission tomography system 200 includes a collecting unit 210, a generating unit 220, a control unit 230, and a learning unit 240.

First, the collection unit 210 collects the positron emission tomography sinogram. The positron emission tomography sinogram represents raw data generated from the positron emission tomography device 100.

Next, the generation unit 220 generates the first emission image and the first attenuation image by applying the MLAA with TOF to the positron emission tomography sinogram.

Here, the MLAA with TOF may include MLAA (A. Rezaei, et al. (2012), Simultaneous reconstruction of activity and attenuation in time-of-flight PET, Trans Med Imaging), MLAA-GMM (A. Mehranina and H., Zaidi (2015), Joint Estimation of Activity and Attenuation in Whole-Body TOF PET/MRI Using Constrained Gaussian Mixture Models, IEEE TRANSACTIONS ON MEDICAL IMAGING), SMLGA-MLAA (S. C. Cade, et al., (2013), Use of measured scatter data for the attenuation correction of single photon emission tomography without transmission scanning, Med Phys), MLACF (M. Defrise, et al. (2014) Transmission-less attenuation correction in time-of-flight PET: analysis of a discrete iterative algorithm, Phys Med Biol), but is not limited thereto.

The control unit 230 selects an image generated by the generation unit 220 as an input image and applies the selected image to the learned deep learning algorithm to generate and provide the final attenuation image.

The control unit 230 may select one or more of the first emission image and the first attenuation image as the input image. For example, the control unit 230 may select only the first attenuation image or select the first emission image and the first attenuation image.

Further, the control unit 230 may select a voxel data group among the first attenuation images as the input image or select the voxel data group in each of the first emission image and the first attenuation image. Here, the voxel data group may include all of a 2D slice, a 3D patch, and a 3D image as a predetermined matrix size, but is not limited thereto.

In addition, the learning unit 240 constructs the learned deep learning algorithm by repeatedly making the deep learning algorithm for generating the final attenuation image be learned.

The learning unit 240 collects the attenuation image obtained through additional scan for the same person based on the positron emission tomography sinogram and makes the deep learning algorithm be learned by using the input image and the obtained attenuation image.

Here, the obtained attenuation image represents an attenuation image obtained by photographing through a medical device different from the positron emission tomography device 100. For example, the obtained attenuation image may include the attenuation images obtained through the medical device such as the computed tomography (CT) or the magnetic resonance imaging (MRI).

As illustrated in FIG. 4, the learning unit 240 includes an image generation unit 241, an error calculation unit 242, and a weight adjustment unit 243.

First, the image generation unit 241 generates a second attenuation image from the first attenuation image through the deep learning algorithm.

Here, the deep learning algorithm is a convolutional neural network (CNN) or a generative adversarial network (GAN) (I. Goodfellow, et al. 2014, Generative Adversarial Network, NIPS) which is known to be specialized to image processing, but is not limited thereto.

Examples of the convolutional neural network (CNN) may include VGGNet (K., Simonyan, A., Zisserman, (2015), Very Deep Convolutional Networks for Large-Scale Image Recognition, ICLR), ResNet (K., He, et al., (2016), Deep Residual Learning for Image Recognition, CVPR), DnCNN (K., Zhang, et al., (2016), Beyond a Gaussian Denoiser: Residual Learning of Deep CNN for Image Denoising, Trans Image Processing), DenseNet (G., Huang, et al., (2017), Densely Connected Convolutional Networks, CVPR), and the like.

In addition, the generative adversarial network (GAN) as a machine running for generating an image similar to original data distribution is used as a technique which may easily and rapidly make a real fake. The generative adversarial network (GAN) learns through competition between two neural network models of a generator G and a discriminator D and generates results. The generator G learns real data for the purpose of generating data close to reality and generates data based on the learned actual data and the discriminator D learns to discriminate whether the data generated by the generator G is true or false.

Next, the error calculation unit 242 calculates an error value between the second attenuation image and the obtained attenuation image.

The error calculation unit 242 may calculate the error value by using a Dice coefficient, a percent error, a Bias and root-mean square error (RMSE), a cost function, etc., but the present invention is not limited thereto.

Then, the weight adjustment unit 243 re-adjusts weights of a plurality of filters included in the deep learning algorithm to repeatedly make the deep learning algorithm be learned. In addition, the weight adjustment unit 243 may control to terminate learning when the error value calculated by the error calculation unit 242 becomes a value equal to or less than a threshold value.

As described above, the learning unit 240 may construct the deep learning algorithm learned so that the first attenuation image generated in the positron emission tomography sinogram matches the obtained attenuation image.

Meanwhile, the positron emission tomography system 200 may be a server, a terminal, or a combination thereof.

The terminal collectively refers to a device having a memory and a processor and having an arithmetic processing capability. For example, the terminal is a personal computer, a handheld computer, a personal digital assistant (PDA), a cellular phone, a smart device, a tablet, and the like.

The server may include a memory storing a plurality of modules, a processor that is connected to the memory, reacts to the plurality of modules, and processes service information provided to the terminal or action information to control the service information, a communication means, and a user interface (UI) display means.

The memory as a device storing information may include various types of memories including a high-speed random access memory, a magnetic disk storage device, a flash memory device, a non-volatile memory including a non-volatile solid-state memory device, and the like.

The communication means transmits/receives the service information or action information to/from the terminal in real time.

The UI display means outputs the service information or action information of the device in real time. The UI display means may be an independent device that directly or indirectly outputs or displays a UI or may be a part of the device.

Hereinafter, a method and a result of learning the deep learning algorithm of the positron emission tomography system 200 will be described in detail with reference to FIGS. 5 to 9B.

Figure 5:
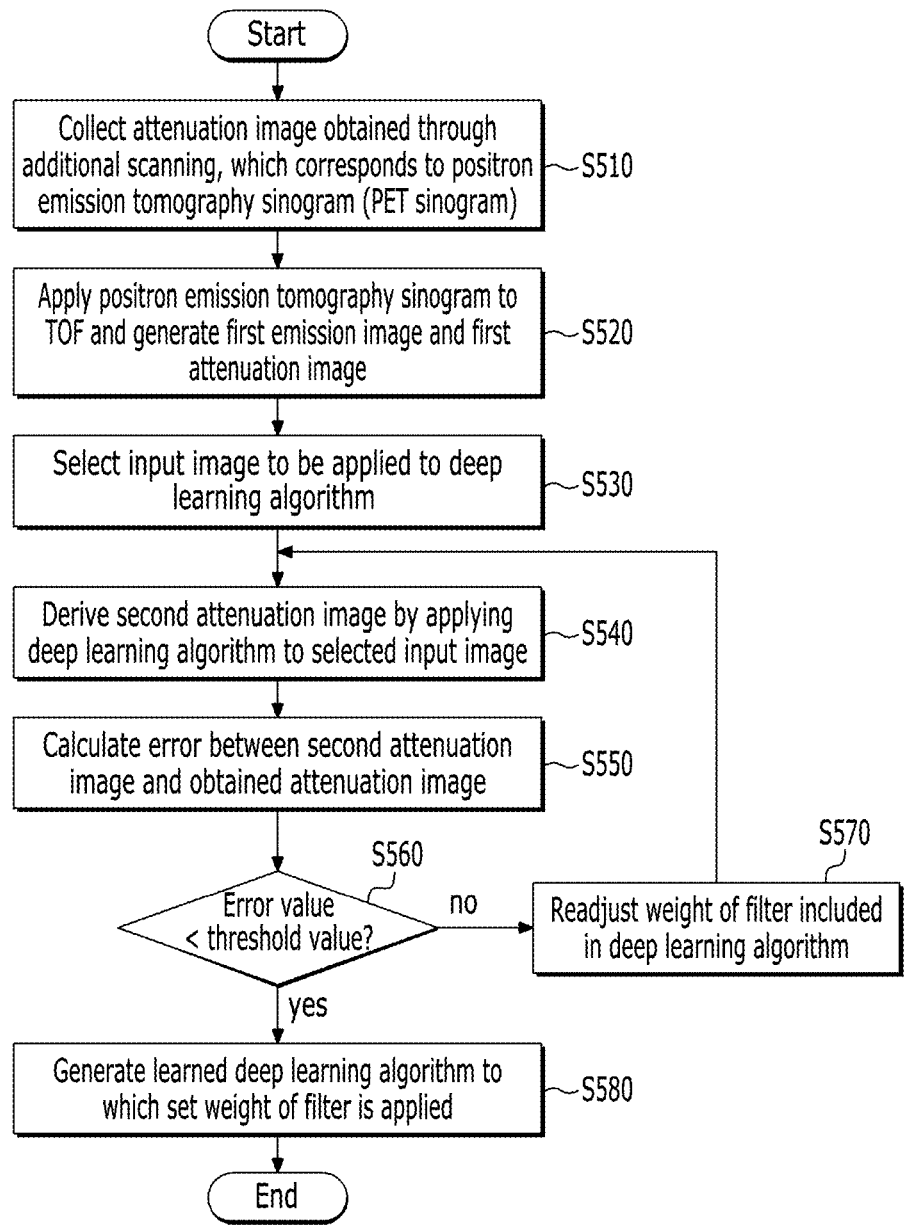
FIG. 5 is a flowchart illustrating a process of learning a deep learning algorithm according to an exemplary embodiment of the present invention.
Figure 6A:
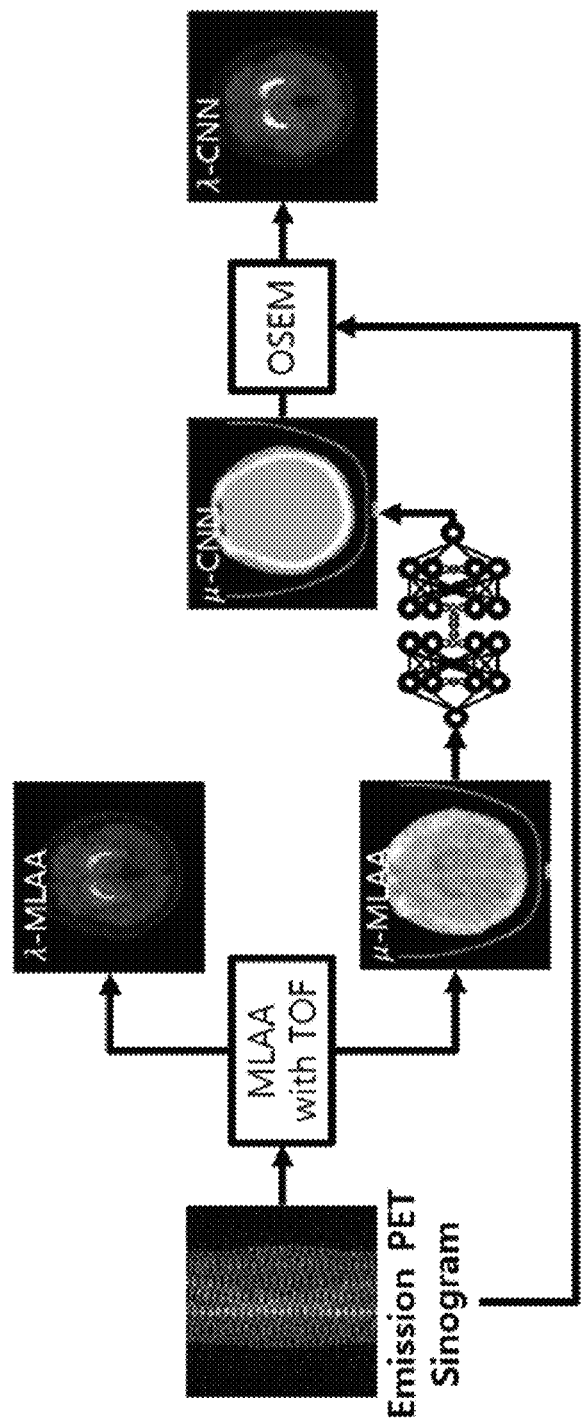
Figure 6B:
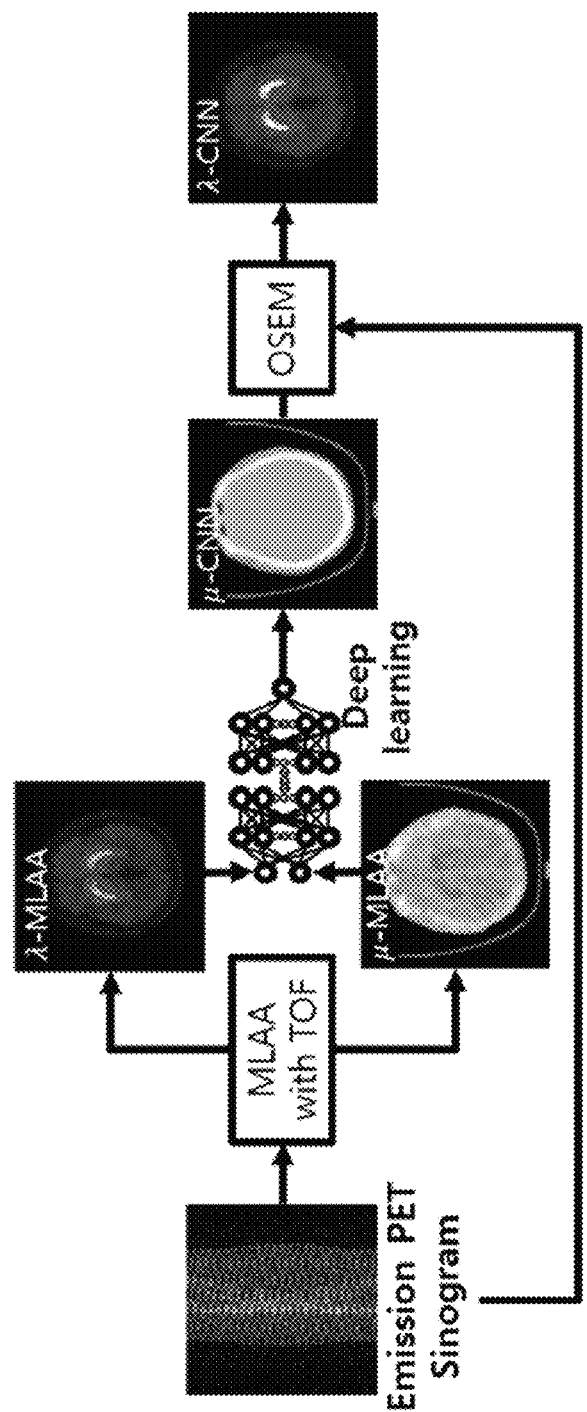

FIG. 5 is a flowchart illustrating a process of learning a deep learning algorithm according to an exemplary embodiment of the present invention and FIGS. 6A, 6B, and 6C are exemplary diagrams for describing an input image of the deep learning algorithm according to an exemplary embodiment of the present invention.

Figure 7:
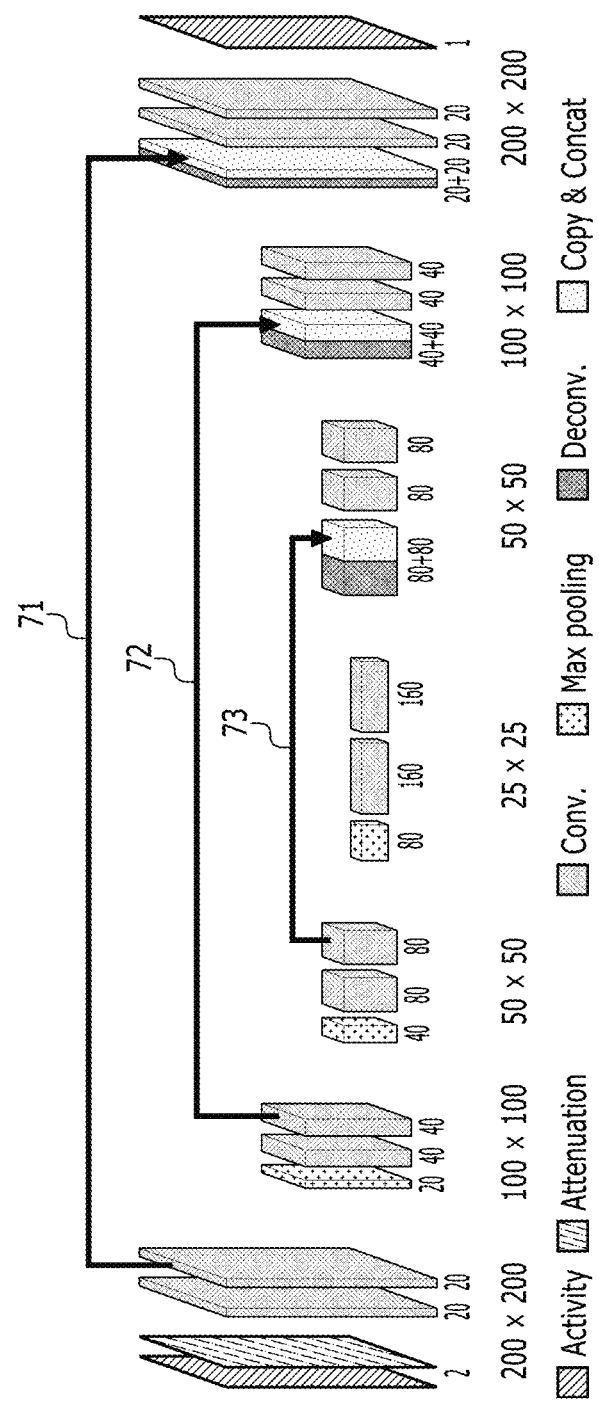
FIG. 7 is an exemplary diagram for describing the deep learning algorithm according to an exemplary embodiment of the present invention.
Figure 8:
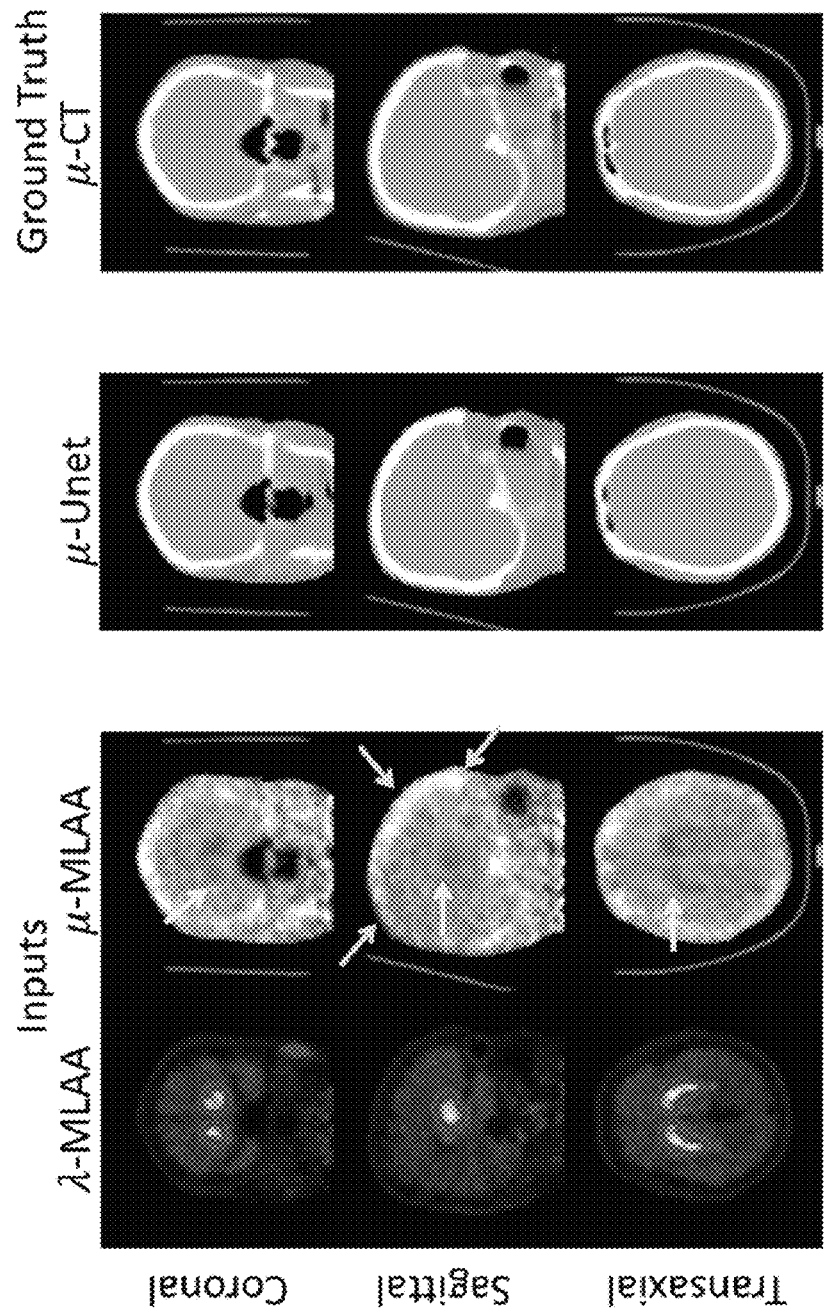
FIG. 8 is an exemplary diagram for comparing a result learned through a U-net deep learning algorithm according to an exemplary embodiment of the present invention.

FIG. 7 is an exemplary diagram for describing the deep learning algorithm according to an exemplary embodiment of the present invention and FIG. 8 is an exemplary diagram for comparing a result learned through a deep learning algorithm according to an exemplary embodiment of the present invention.

As illustrated in FIG. 5, the positron emission tomography system 200 collects an attenuation image obtained through additional scan to correspond to a positron emission tomography sinogram (S510).

The positron emission tomography system 200 collects attenuation images obtained by shots of a positron emission tomography sinogram and a CT medical device for the same person.

In this case, the positron emission tomography system 200 may collect shot images by interlocking with each medical device in real time and collect an image by accessing a separate database (not illustrated).

Next, the positron emission tomography system 200 applies the image to an MLAA with TOFTOF to generate a first emission image and a first attenuation image (S520). In addition, the positron emission tomography system 200 selects an input image to be applied to the deep learning algorithm (S530).

For example, the positron emission tomography system 200 may select only the first attenuation image as the input image or select the first emission image and the first attenuation image as the input image.

FIG. 6A illustrates a process in which the positron emission tomography system 200 selects a first attenuation image (μ-MLAA) as an input image and applies the selected first attenuation image to a deep learning algorithm (CNN) to generate a final attenuation image (μ-CNN). In addition, FIG. 6B illustrates a process in which the positron emission tomography system 200 selects a first emission image (λ-MLAA) and the first attenuation image (μ-MLAA) as the input image and applies the selected first emission image and first attenuation image to the deep learning algorithm (CNN) to generate the final attenuation image (μ-CNN).

Meanwhile, as shown in FIG. 6C, the positron emission tomography system 200 may select a two-dimensional slice type as the input image and generate the final attenuation image with a two-dimensional slice through the deep learning algorithm.

As described above, the positron emission tomography system 200 may select the first attenuation or the first emission image, and the first attenuation image as a plurality of voxel data groups in the form of a three-dimensional patch.

In other words, the positron emission tomography system 200 may select a type of image to be input into a learning algorithm and select a form such as the 2D slice, the 3D patch, or an entire 3D image for the selected image.

Next, the positron emission tomography system 200 applies the selected input image to the deep learning algorithm to generate the second attenuation image (S540).

As illustrated in FIG. 7, the positron emission tomography system 200 applies the input image to the deep learning algorithm to make the deep learning algorithm be learned from left to right.

FIG. 7 illustrates a process of learning through the U-net deep learning algorithm among various deep learning algorithms including CAE, U-net, Hybrid, and the like, in which a first attenuation image and a first emission image (activity) are selected as the input image in a 2D slice type.

In addition, in FIG. 7, each box shape shows a multi-channel function map and the number and the size associated with each multi-channel function map as one example may be easily designed and changed by a manager later.

First, the positron emission tomography system 200 generates a plurality of feature maps from the input image using a filter of the deep learning algorithm.

As illustrated in FIG. 7, the positron emission tomography system 200 generates several feature maps through a line using the filter in sizes (200*200) of the first attenuation image and the first emission image (activity). Here, the number of feature maps is two and each of the feature maps is illustrated as 20 sheets, but is not limited thereto and may be changed and designed by the manager later.

Next, the positron emission tomography system 200 generates a downsized sample from the feature map at a predetermined ratio (Max pooling 20, 100*100). Such a process is called pooling, and Max pooling using a maximum value is used in FIG. 7, but the present invention is not limited thereto.

In addition, the positron emission tomography system 200 generates several feature maps through the line using the filter in the downsized sample (100*100).

Again, the positron emission tomography system 200 generates a downsized sample by using a plurality of feature maps at a predetermined ratio (Max pooling 40, 50*50). In addition, the positron emission tomography system 200 generates several feature maps through the line using the filter in the downsized sample (50*50).

In other words, the positron emission tomography system 200 repeatedly generates the feature map and performs downsizing until the size of the downsized sample reaches a predetermined reference size.

In addition, when a size (Max pooling 80, 25*25) of the downsized sample reaches a predetermined reference size, the positron emission tomography system 200 uses the plurality of feature maps and upsizes the corresponding feature maps at a predetermined ratio (Deconv 80, 50*50) and collects the downsized feature maps (50*50) having a size which is the same as that of the upsized sample.

The positron emission tomography system 200 collects samples (Copy & Concat) before downsizing and combines the collected samples with the upsized sample in order to compensate for a tendency of smoothing the feature map generated through the filter.

As illustrated in 73 of FIG. 7, the feature maps of the same size are collected and combined from the step of upsizing the sample and the feature maps are generated from the combined samples. In addition, the plurality of feature maps are used and upsized at a predetermined ratio (Deconv 40, 100*100) and the feature maps having the same size are collected and combined (72) and the feature maps are generated from the combined samples.

The positron emission tomography system 200 generates the feature map by repeating the process until the size of the feature map becomes equal to the size of a first input image. In addition, the positron emission tomography system 200 may generate the second attenuation image which has the same size as the first input image.

Meanwhile, the positron emission tomography system 200 may not collect the feature map of the same size when the size of the upsized sample is the same as the initial image input size, such as a hybrid deep learning algorithm. In other words, it is possible to exclude the step (71 in FIG. 7) of collecting an initially generated feature map according to a possibility that the initially generated feature map will include a lot of noise and combining the collected feature map with the upsized sample.

Next, the positron emission tomography system 200 calculates an error between the second attenuation image and the obtained attenuation image (S550).

The positron emission tomography system 200 may calculate the error value by using a Dice coefficient, a percent error, a Bias and root-mean square error (RMSE), a cost function, etc.

For example, the positron emission tomography system 200 may calculate the Dice coefficient between the second attenuation image generated through the deep learning algorithm and the obtained attenuated image through Equation 1 and compare similarities between the two images.

In other words, the similarity may be compared using the Dice coefficient that measures an overlap of bones and air regions in each image.

$$D_{type} = \frac{2 \times n(\mu_{type}^{PET} \cap \mu_{type}^{CT})}{n(\mu_{type}^{PET}) + n(\mu_{type}^{CT})}$$ [Equation 1]

$$type = \begin{cases} bone \\ air \end{cases}$$

A value of the Dice coefficient has values from 0 to 1 and as the value of the Dice coefficient is closer to 0, the similarity is low and as the value of the Dice coefficient is closer to 1, the similarity is high.

In this case, when the positron emission tomography system 200 calculates the similarity by using the Dice coefficient, the positron emission tomography system 200 may estimate the error based on the calculated similarity.

Meanwhile, the positron emission tomography system 200 may calculate the error by setting a region of interest in the image and calculating the percent error in the second attenuation image and the obtained attenuation image.

Besides, the positron emission tomography system 200 may include various methods capable of measuring the error or similarity between the second attenuation image and the obtained attenuation image.

In addition, the positron emission tomography system 200 compares the calculated error value and a predetermined threshold value (S560).

In this case, the positron emission tomography system 200 readjusts the weight of the filter included in the deep learning algorithm when the error value is larger than the predetermined threshold (S770).

Meanwhile, in a process of initially learning the deep learning algorithm, weights applied to a plurality of filters are randomly initialized, and the respective weights are readjusted so that the second attenuation image generated through learning approaches the obtained attenuation image.

The positron emission tomography system 200 then returns to step S540 with the deep learning algorithm that includes the readjusted weight of the filter. As described above, the positron emission tomography system 200 may enhance a matching degree between the second attenuation image generated while repeating steps S540 to S570 and the obtained attenuation image ($\mu$-CT).

Meanwhile, when the error value is smaller than the predetermined threshold value in step S560, the positron emission tomography system 200 generates the learned deep learning algorithm to which the weight of the filter is applied (S580). As described above, the positron emission tomography system 200 may construct the learned deep learning algorithm and store and manage the learned algorithm.

In this case, positron emission tomography system 200 may make a plurality of deep learning algorithms be learned and select and construct a deep learning algorithm having a smallest error from the obtained attenuation image (Ground Truth, $\mu$-CT) which becomes a criterion.

FIG. 8 is an exemplary diagram illustrating an input image (Inputs, $\lambda$-MLAA, $\mu$-MLAA) and the final attenuation image ($\mu$-Unet) of the deep learning algorithm and the obtained attenuation image (Ground Truth, $\mu$-CT).

As illustrated in FIG. 8, it can be seen that in a coronal, a sagittal, and a transaxial of the brain, in the case of the first emission image ($\lambda$-MLAA) and the first attenuation image ($\mu$-MLAA) generated by the MLAA with TOF, the images themselves have a lot of noise and a portion (red system color) in which the activity is highly exhibited in the first emission image ($\lambda$-MLAA) appears in the first attenuation image ($\mu$-MLAA).

In detail, a plurality of arrows illustrated in FIG. 8 as regions that are not well estimated by the MLAA algorithm and show a large difference from the CT indicate a greatly improved region in the final attenuation image ($\mu$-Unet) generated by the deep learning algorithm.

First, a yellow arrow indicates a crosstalk artifact in which a region in which the activity is highly exhibited in the emission image appears in the attenuation image and is distorted. When $\mu$-MLAA and $\mu$-CT are compared with each other, it can be seen that a portion indicated by a yellow arrow is estimated to be low in $\mu$-MLAA and displayed to be relatively dark. On the contrary, in $\mu$-Unet, it can be seen that such a phenomenon is improved.

Next, an orange arrow indicates a skull region and in the $\mu$-MLAA, it can be seen that there is a tendency in which an anterior part of the skull is estimated to be thicker than the $\mu$-CT and a posterior part is estimated to be thinner than the $\mu$-CT. On the contrary, it can be seen that the thickness in the $\mu$-Unet is improved to a thickness almost similar to the thickness in the $\mu$-CT. As described above, an image quality of the final attenuation image ($\mu$-Unet) is more distinct than the image quality of the first attenuation image ($\mu$-MLAA) through the U-net deep learning algorithm and it can be seen that a quantitative error is minimized due to the noise and artifact described above. Moreover, it can be seen that the final attenuation image ($\mu$-Unet) is very similar to the attenuation image ($\mu$-CT) obtained through the CT shot.

Table 1 below shows a result of calculating a similarity between the final attenuation image generated through the deep learning algorithm by using the Dice coefficient and the obtained attenuation image by the positron emission tomography system 200.

TABLE 1

| Method | Whole Head | | Cranial Region | |
| --- | --- | --- | --- | --- |
|  | $D_{bone}$ | $D_{air}$ | $D_{bone}$ | $D_{air}$ |
| MLAA | 0.374 ± 0.058 | 0.317 ± 0.070 | 0.399 ± 0.063 | 0.426 ± 0.062 |
| CNN (CAE) | 0.717 ± 0.047 | 0.513 ± 0.057 | 0.747 ± 0.047 | 0.523 ± 0.063 |
| CNN (U-net) | 0.787 ± 0.042 | 0.575 ± 0.047 | 0.801 ± 0.043 | 0.580 ± 0.053 |
| CNN (Hybrid) | 0.794 ± 0.037 | 0.718 ± 0.048 | 0.810 ± 0.038 | 0.738 ± 0.044 |

Table

Referring to Table 1, the first attenuation image and the obtained attenuation image are compared with each other based on the attenuation images measured in a whole head and a cranial region and it can be seen that the Dice coefficient is generally larger in the attenuation image showing the cranial region than in the attenuation image showing the whole head.

In addition, it can be seen that the similarity of the final attenuation image generated in CNN (Hybrid), CNN (U-net), or CNN (CAE) with the obtained attenuation image is higher than the similarity of the first attenuation image generated in MLAA.

Hereinafter, the first attenuation image generated through the MLAA with TOF, final attenuation images generated by using various deep learning algorithms, and the attenuation image obtained through the CT are compared with each other by using FIG. 9.

Figure 9A:
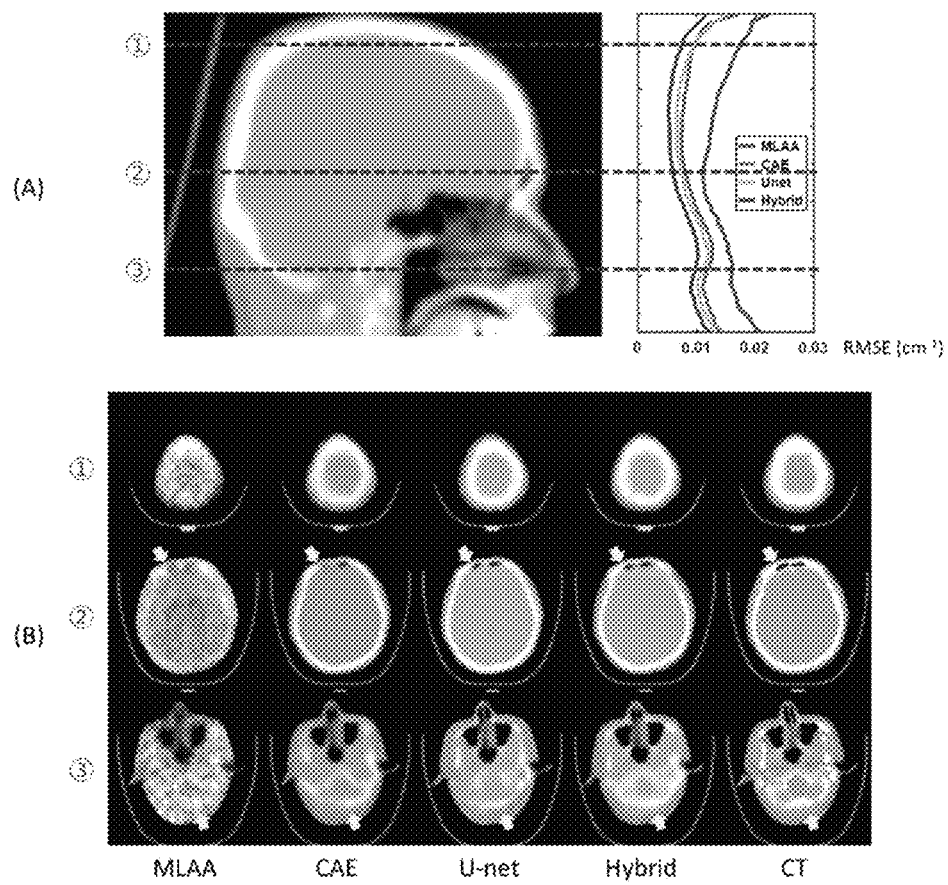
FIGS. 9A and 9B are exemplary diagrams for comparing images generated through a plurality of deep learning algorithms according to an exemplary embodiment of the present invention.
Figure 9B:
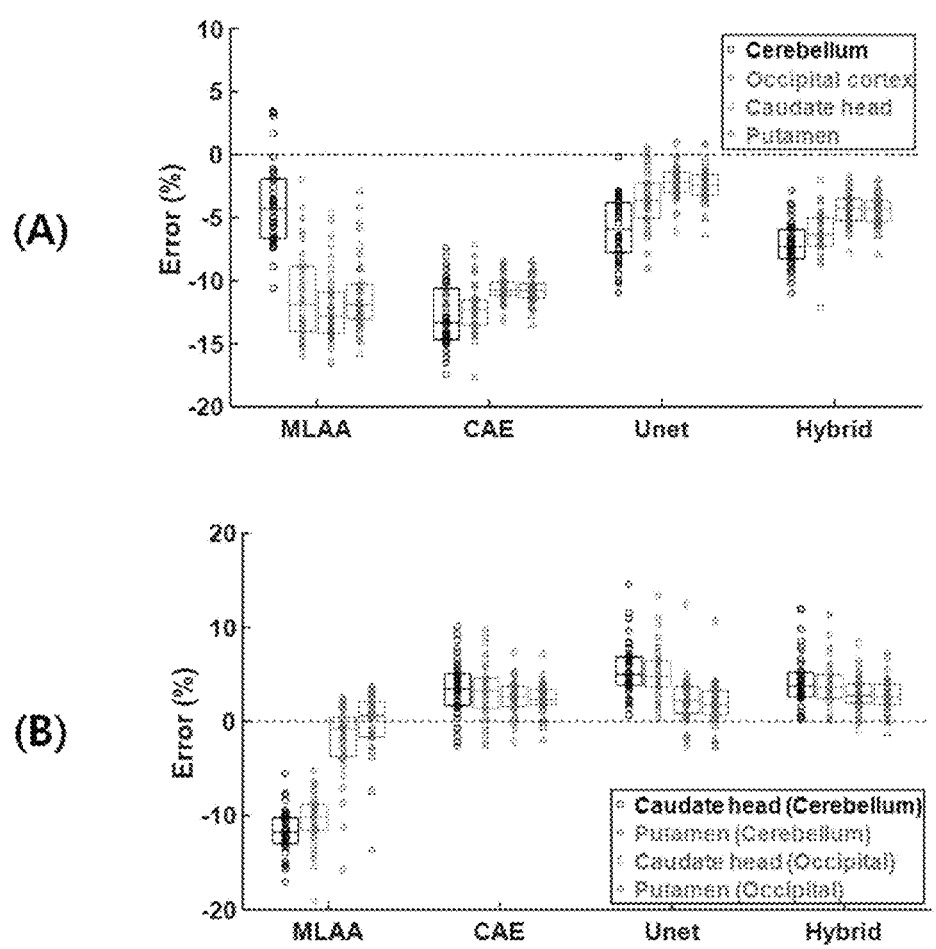

FIGS. 9A and 9B are exemplary diagrams for comparing images generated through a plurality of deep learning algorithms according to an exemplary embodiment of the present invention.

First, as illustrated in (A) of FIG. 9A, referring to a graph shown by generating an RMSE error value for the image of Sagittal, it can be seen that an image having a largest error is the first attenuation image ($\mu$-MLAA) at a rightmost side and subsequent images are CAE, U-net, and Hybrid.

In particular, when the attenuation images of MLAA and Hybrid are compared with each other, it can be seen that the error which appears in the attenuation image MLAA is reduced to 50% or less in the attenuation image generated by Hybrid.

In (B) of FIG. 9A, ①, ②, and ③ as results corresponding to respective locations of ①, ②, and ③ in (A) of FIG. 9A show the first attenuation image (μ-MLAA) for the transaxial of the brain and the attenuation images obtained by CAE, U-net, Hybrid, and the CT image as the attenuation image. Referring to (B) of FIG. 9A, it can be seen that the second attenuation image generated by the Hybrid deep learning algorithm is most similar to the obtained attenuation image (CT).

(A) of FIG. 9B is a graph showing the percent error calculated with respect to the first attenuation image (μ-MLAA) and the attenuation image (CAE, U-net, and Hybrid) through the deep learning algorithm. In addition, (B) of FIG. 9B is a graph of measuring a specific binding ratio with respect to the first attenuation image (μ-MLAA) and the attenuation image (CAE, U-net, and Hybrid) through the deep learning algorithm and showing the calculated percent error.

(A) of FIG. 9B illustrates a value obtained by setting the region of interest with respect to four regions, i.e., cerebellum, occipital cortex, caudate head, and putamen, which is a subcortical region and calculating the percent error from the attenuation image (CT) obtained with respect to each region.

In (A) of FIG. 9B, a long vertical box indicates a standard deviation in each calculated percent error value and a horizontal bar in the long vertical box indicates a median value.

In the comparison based on the median value in (A) of FIG. 9B, it can be seen that the attenuation image of MLAA and the attenuation image by CAE have the largest error and a percent error value between the attenuation images through the U-net and Hybrid deep learning algorithms is small.

Next, (B) of FIG. 9B illustrates a value obtained by measuring the specific binding ratio with respect to a region which is the same as the region of interest selected in (A) of FIG. 9B and calculating the percent error from the attenuation image (CT) obtained for each region.

In (B) of FIG. 9B, the long vertical box indicates a standard deviation in each calculated percent error value and the horizontal bar in the long vertical box indicates the median value.

In the comparison based on the median value in (B) of FIG. 9B, it can be seen that the first attenuation image of MLAA shows an error of 10% or more, while all of the attenuation images (CAE, U-net, and Hybrid) through the deep learning algorithm have a very small error of approximately 5%.

As described above, it can be seen that the final attenuation image generated through the deep learning algorithm proposed by the present invention has a very high similarity with the obtained attenuation image (CT) and the noise and the error are greatly reduced as compared with the first attenuation image of the MLAA.

Hereinafter, a process of generating a final attenuation image and a final emission image using the positron emission tomography sinogram collected in real time using the learned deep learning algorithm will be described in detail.

Figure 10:
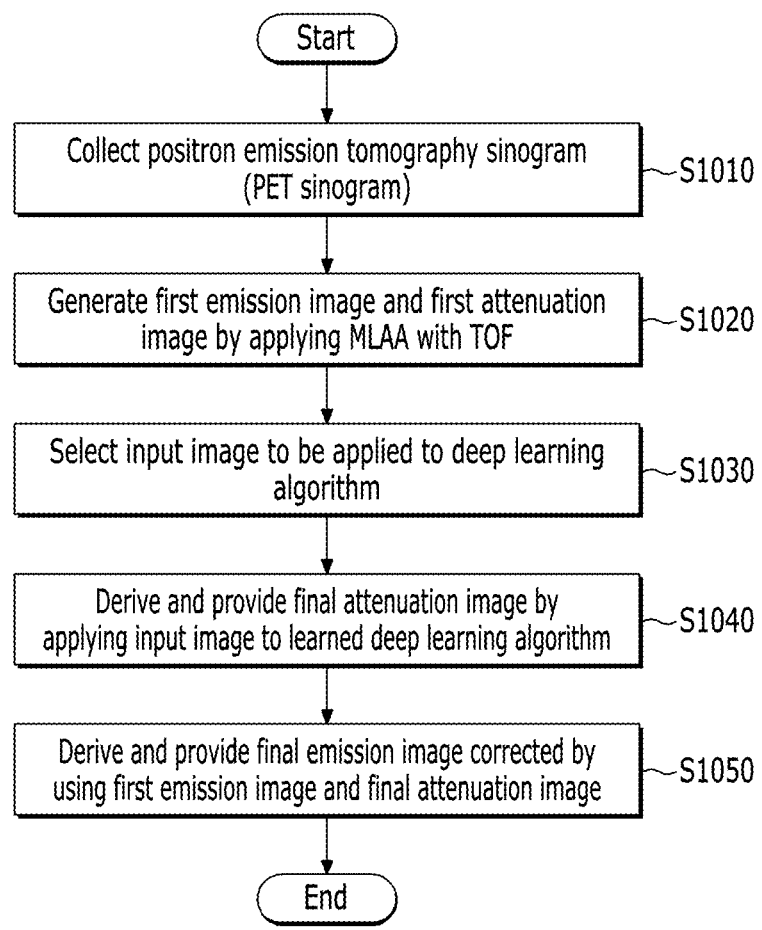
FIG. 10 is a flowchart illustrating a method for reconstructing an image in a positron emission tomography system according to an exemplary embodiment of the present invention.

FIG. 10 is a flowchart illustrating a method for reconstructing an image in a positron emission tomography system according to an exemplary embodiment of the present invention.

The positron emission tomography system 200 collects the positron tomography sinogram (S1010). In addition, the positron emission tomography system 200 applies the image to the MLAA with TOF to generate a first emission image and a first attenuation image (S1020).

In this case, the positron emission tomography system 200 may collect the first emission image and the first attenuation image generated by the MLAA with TOF in the positron tomography sinogram without collecting the positron tomography sinogram.

In other words, in the positron emission tomography system 200, a step of collecting the first emission image and the first attenuation image generated by the MLAA with TOF in an external device or a database which is interlocked may be replaced without going through steps S1010 and S1020.

Next, the positron emission tomography system 200 selects an input image to be applied to the deep learning algorithm (S1030).

The positron emission tomography system 200 may select a type of image input into a learning algorithm and select a type such as the 2D slice, the 3D patch, or the entire 3D image for the selected image.

Hereinafter, the positron emission tomography system 200 will be described by assuming each of a case (CNN1) of selecting the voxel data group from the first attenuation image and a case (CNN2) of selecting the voxel data group from the first emission image and the first attenuation image.

Next, the positron emission tomography system 200 applies the input image to the learned deep learning algorithm to generate and provide the final attenuation image (S1040).

The positron emission tomography system 200 may select a corresponding learned deep learning algorithm based on the type and the form of the selected input image.

Figure 11:
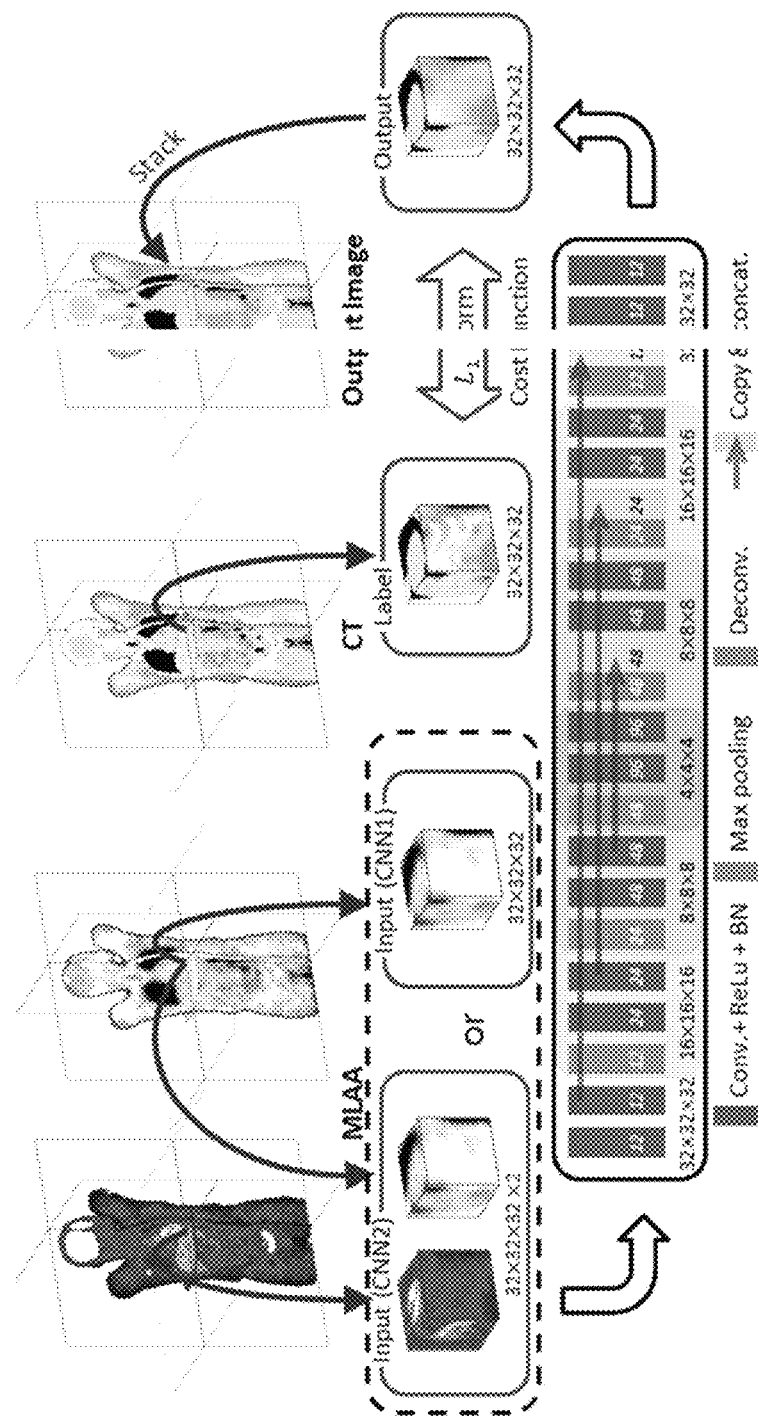
FIG. 11 is an exemplary diagram illustrating a deep learning algorithm of learning a 3D patch by an input image and an output image according to an exemplary embodiment of the present invention.

FIG. 11 is an exemplary diagram illustrating a deep learning algorithm of learning a 3D patch by an input image and an output image according to an exemplary embodiment of the present invention.

As illustrated in FIG. 11, the positron emission tomography system 200 may select the voxel data group in each of the first emission image and the first attenuation image generated through the MLAA with TOF.

Here, the deep learning algorithm may be divided into the case (CNN1) where the 3D patch is selected from the first attenuation image as the input image of the deep learning algorithm and the case (CNN2) where the 3D patch is selected from each of the first emission image and the first attenuation image.

Further, all inputs and labels may be used in a matrix size of 32*32*32, which is not limited to the shape of the cube in one example, and may be easily changed and designed later.

Similarly to the deep learning algorithm learning method described through FIG. 5, the positron emission tomography system 200 calculates the feature map in the input image and adjusts the weight of the filter of the deep learning algorithm so as to approach the attenuation image obtained from the CT image while adjusting the size.

The positron emission tomography system 200 may calculate the error value by using the cost function between the 3D patch type second attenuation image calculated through the deep learning algorithm and the attenuation image obtained from the CT image and repeats learning while readjusting the weight of the filter of the deep learning algorithm so as to minimize the cost function.

As described above, the positron emission tomography system 200 may generate the final attenuation image of the 3D patch type through the 3D patch type input image by using the learned deep learning algorithm.

Figure 12:
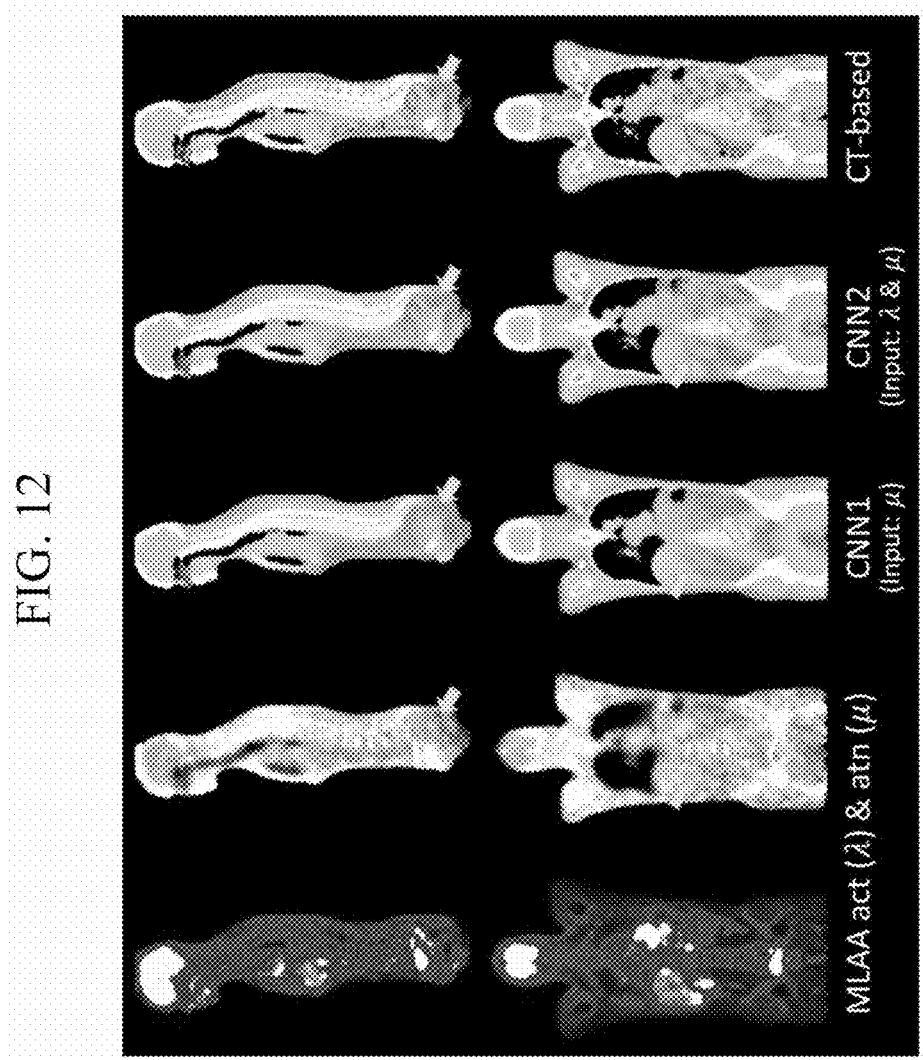
FIG. 12 is an exemplary diagram illustrating the attenuation image reconstructed by using the 3D patch through the deep learning algorithm according to an exemplary embodiment of the present invention.

In this case, the positron emission tomography system 200 derives the final attenuation image in the type of the 3D image regardless of whether the type of the input is the 2D slice or the 3D patch. For example, when the input type is the 2D slice, the positron emission tomography system 200 may generate the 3D image as the final attenuation image by combing a plurality of 2D slices. FIG. 12 is an exemplary diagram illustrating the attenuation image reconstructed by using the 3D patch through the deep learning algorithm according to an exemplary embodiment of the present invention.

As illustrated in FIG. 12, it can be seen that in the first emission image (MLAA act(λ)) and the first attenuation image (MLAA atn(μ)) generated through the MLAA with TOF, the noise and the crosstalk artifact are significantly exhibited.

Further, it can be seen that when the case (CNN1) of selecting the 3D patch in the first attenuation image and the case (CNN2) of selecting the 3D patch in each of the first emission image and the first attenuation image are compared with the attenuation image (CT-based) obtained from the CT image, a higher similarity with the CT-based image in CNN2 is provided than in CNN1.

In detail, it can be seen that the noise is significantly reduced and skeleton identification is enhanced in CNN2 as compared with CNN1. Therefore, it can be seen that a scheme (CNN2) applied to the deep learning algorithm learned by using both the first emission image and the first attenuation image has a better result in terms of anatomical details.

Meanwhile, the Dice coefficient of the attenuation image obtained from MLAA, CNN1, CNN2, and the CT image is calculated through Equation 2 below as shown in Table 2 below.

$$D_{type} = \frac{2 \times n(\mu_{type}^{method} \cap \mu_{type}^{CT})}{n(\mu_{type}^{method}) + n(\mu_{type}^{CT})} \quad \text{[Equation 2]}$$

$$\text{method} = \begin{cases} MLAA \\ CNN1 \\ CNN2 \end{cases}$$

$$\text{type} = \begin{cases} \text{bone} \\ \text{water} \\ \text{fat} \\ \text{lung} \end{cases}$$

TABLE 2

| Method | $D_{bone}$ | $D_{water}$ | $D_{fat}$ | $D_{lung}$ n = 20 |
|---|---|---|---|---|
| MLAA | 0.363 ± 0.068 | 0.686 ± 0.030 | 0.587 ± 0.037 | 0.328 ± 0.156 |
| CNN1 | 0.722 ± 0.061 | 0.854 ± 0.024 | 0.807 ± 0.046 | 0.857 ± 0.052 |
| CNN2 | 0.771 ± 0.066 | 0.883 ± 0.027 | 0.842 ± 0.056 | 0.863 ± 0.053 |

The closer the value of the Dice coefficient is to 1, the higher the similarity. Thus, it can be seen from Table 2 that the final attenuation image generated by CNN2 has the highest similarity.

As described above, it can be seen that the final attenuation image generated through the deep learning algorithm also has a very high similarity with the obtained attenuation image (CT) by using the 2D slice and the 3D patch type and the noise and the error are greatly reduced as compared with the first attenuation image of the MLAA.

Next, the positron emission tomography system 200 generates and provides the final emission image corrected by using the first emission image and the final attenuation image (S1050).

The positron emission tomography system 200 may reconstruct the attenuated and corrected final emission image by using a reconstruction algorithm (OSEM).

Figure 13:
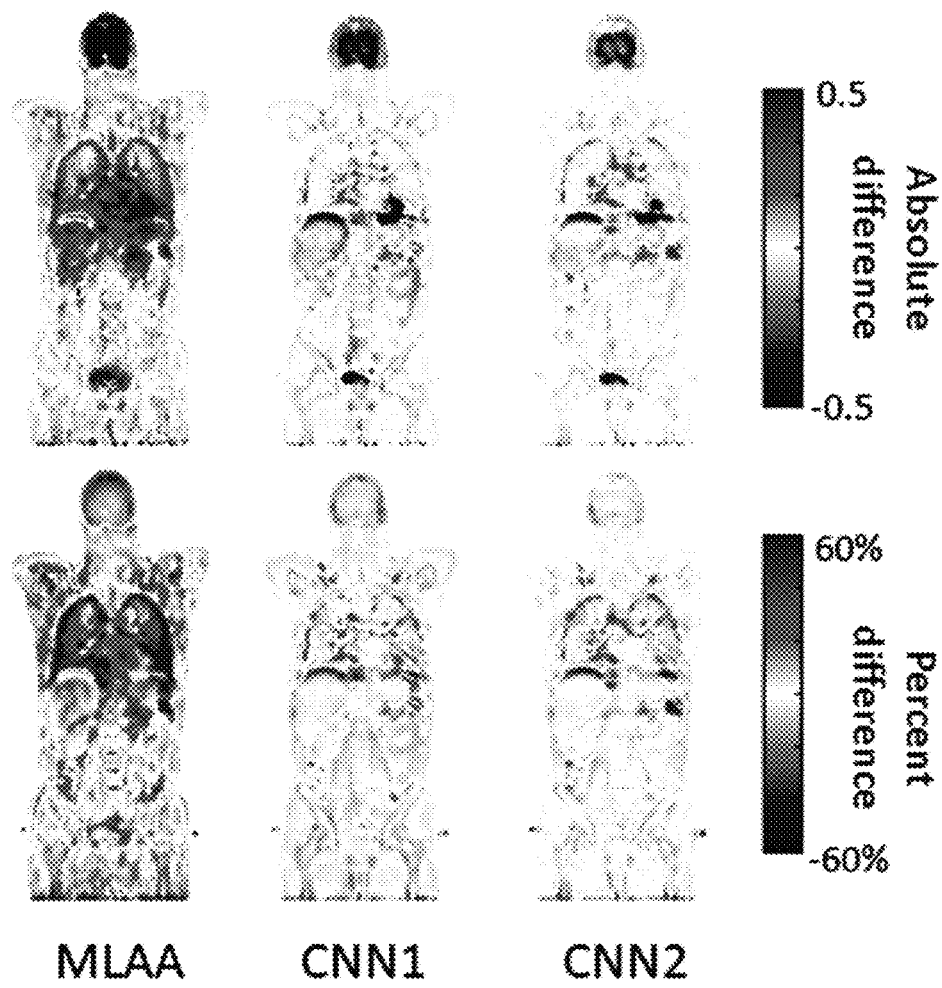
FIG. 13 is an exemplary diagram illustrating an SUV error measured with respect to an emission image reconstructed by using the 3D patch according to an exemplary embodiment of the present invention.

FIG. 13 is an exemplary diagram illustrating an SUV error measured with respect to an emission image reconstructed by using the 3D patch according to an exemplary embodiment of the present invention.

FIG. 13 is a diagram of measuring an SUV error in an emission image reconstructed by using Equation 3 and comparing accuracy of attenuation correction by using MLAA and CNN results.

$$\text{Absolute difference} = \lambda_* - \lambda_{CT} \quad \text{[Equation 3]}$$

$$\text{Percent difference} = \frac{\lambda_* - \lambda_{CT}}{\lambda_{CT}} \times 100$$

Here, λ* represents one emission image among MLAA, CNN1, or CNN2.

As illustrated in FIG. 13, it can be seen that in both CNN1 and CNN2, the error may be remarkably reduced as compared with CT based attenuation correction and an absolute difference and a percent difference are the smallest in CNN2.

Figure 14:
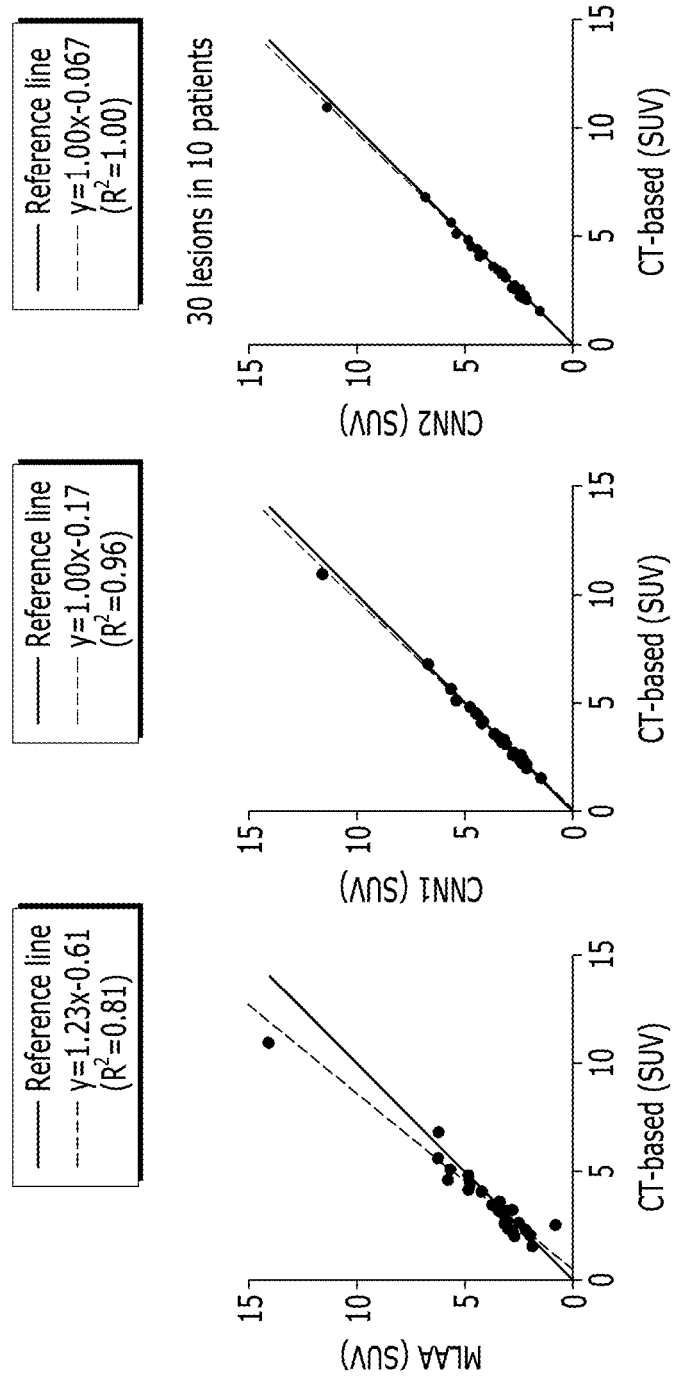
FIG. 14 is an exemplary diagram of comparing ROI based SUV with respect to a reconstructed image and a CT based image according to an exemplary embodiment of the present invention.

Next, FIG. 14 is an exemplary diagram of comparing ROI based SUV with respect to a reconstructed image and a CT based image according to an exemplary embodiment of the present invention.

FIG. 14 illustrates a result of comparing SUV based on a region of interest (ROI) with bone lesions. Specifically, FIG. 14 as graphs showing a correlation between each of MLAA, CNN1, or CNN2 image for the region of interest (ROI) with the bone lesions and the CT based image illustrated that the correlation is higher as being closer to a reference line Y=X.

It can be seen that CNN1 and CNN2 have better consistency with respect to the reference line Y=X than MLAA. In particular, it can be seen that a value of the correlation of CNN2 is higher.

Hereinafter, as an image reconstruction method according to another embodiment of the present invention, a process of generating a final attenuation image using NAC (nonattenuation-corrected PET) image, the first attenuation image and the first emission image.

Here, the NAC image refers to an NAC PET activity images reconstructed without attenuation correction of the sinogram.

Figure 15A:
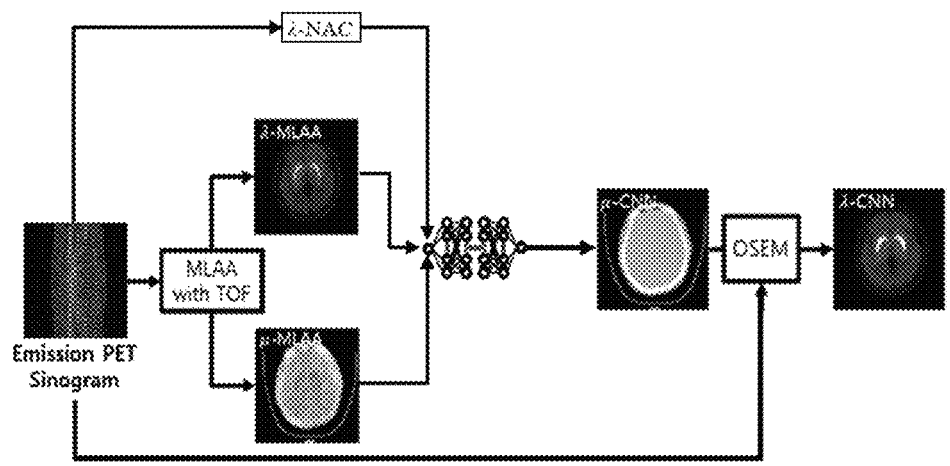
FIGS. 15A and 15B are exemplary diagrams for describing input image of the deep learning algorithm according to the other exemplary embodiment of the present invention.
Figure 15B:
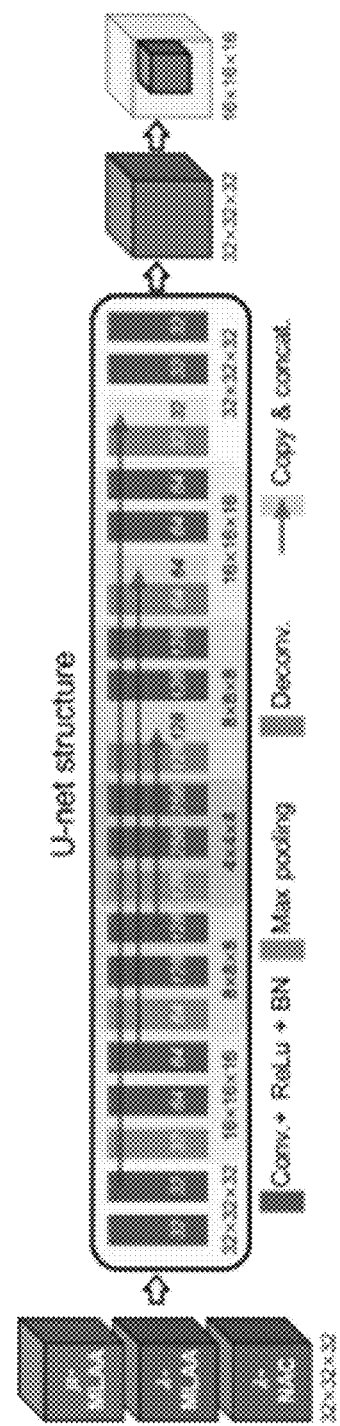

FIGS. 15A and 15B are exemplary diagrams for describing input image of the deep learning algorithm according to the other exemplary embodiment of the present invention.

As illustrated in FIG. 15A the positron emission tomography system 200 selects first emission image (λ-MLAA), the first attenuation image (μ-MLAA), and the NAC image as input images of a deep learning algorithm (CNN).

The positron emission tomography system 200 may acquire a NAC image (NAC PET activity image, λ-NAC) through a subset expectation maximization (OSEM) algorithm arranged in a PET scan image.

In addition, the positron emission tomography system 200 generates a first emission image and a first attenuation image in the positron emission tomography sinogram collected through an MLAA with TOFF.

In this case, in order to solve the non-unique a global scaling problem in the simultaneous reconstruction algorithm (MLAA), a boundary constraint may be applied during the attenuation map estimation in the MLAA.

As described above, the positron emission tomography system 200 applies the first attenuation image, the first emission image and NAC image to a learned deep running algorithm to provide a final attenuation image.

In addition, 15B shows a deep learning algorithm (CNN3, U-net) for deriving a final attenuation image ($\mu$-CNN) by inputting a first emission image ($\lambda$-MLAA), a first attenuation image ($\mu$-MLAA), and a NAC image ($\lambda$-NAC).

As illustrated in 15B, when each voxel data group is input from each of the three input images, iterative learning is performed in the same manner as in the deep learning algorithm learning method described above.

Specifically, the positron emission tomography system 200 is trained by designing deep learning algorithms (CNN3, U-net) to predict the ground-truth CT-derived $\mu$-map ($\mu$-CT) from $\lambda$MLAA, $\mu$-MLAA, and $\lambda$-NAC.

Here, the inputs to the CNN are the 32×32×32 matrix patches randomly extracted from $\lambda$-MLAA, $\mu$-MLAA, and $\lambda$-NAC, and labels are same sized patches from $\mu$-CT at the corresponding location. Each convolution and deconvolution layer is composed of a 3×3×3 kernel, except for the last layer in which a 1×1×1 circuit is used for scaling purposes, and these configurations can be easily changed and designed later.

The positron emission tomography system 200 calculates the feature map in the input image and adjusts the weight of the filter of the deep learning algorithm so as to approach the attenuation image obtained from the CT image while adjusting the size. The positron emission tomography system 200 may calculate the error value by using the cost function between the 3D patch type second attenuation image calculated through the deep learning algorithm and the attenuation image obtained from the CT image and repeats learning while readjusting the weight of the filter of the deep learning algorithm so as to minimize the cost function.

As described above, the positron emission tomography system 200 may generate the final attenuation image of the 3D patch type through the 3D patch type input image by using the learned deep learning algorithm.

Figure 16:
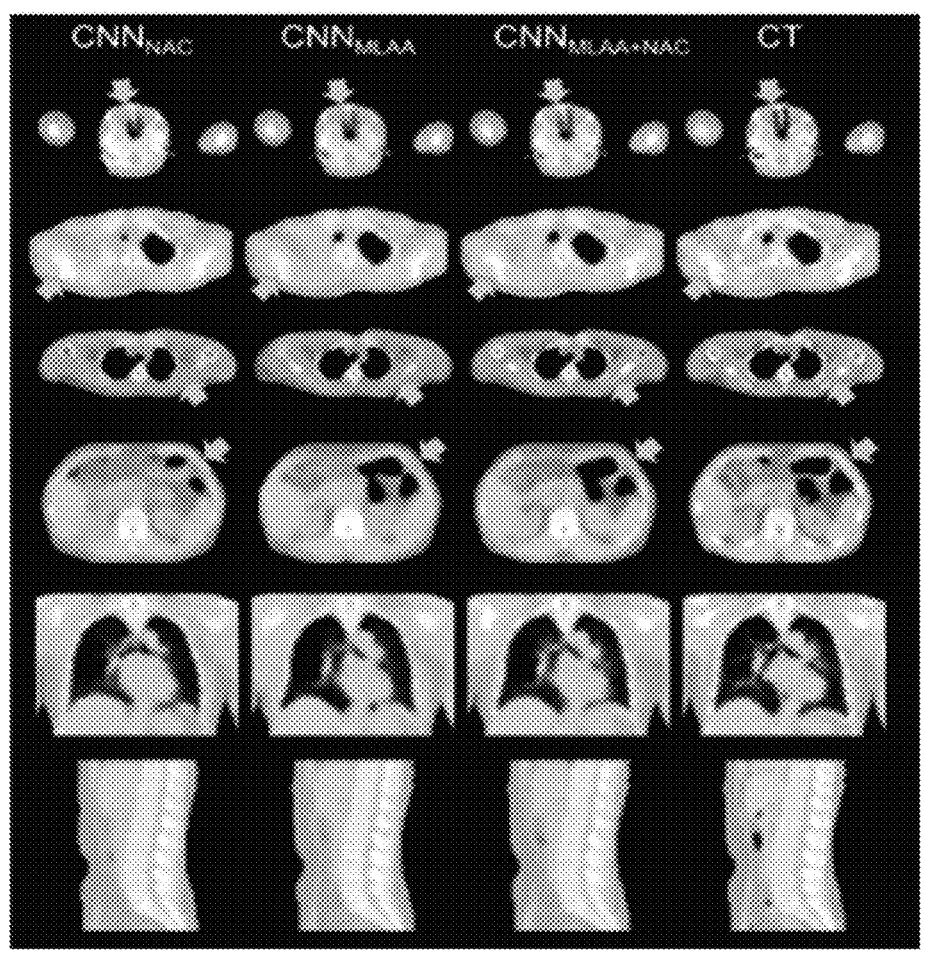
FIGS. 16 and 17 are exemplary diagrams of comparing images generated through input image of deep learning algorithms according to an exemplary embodiment of the present invention.
Figure 17:
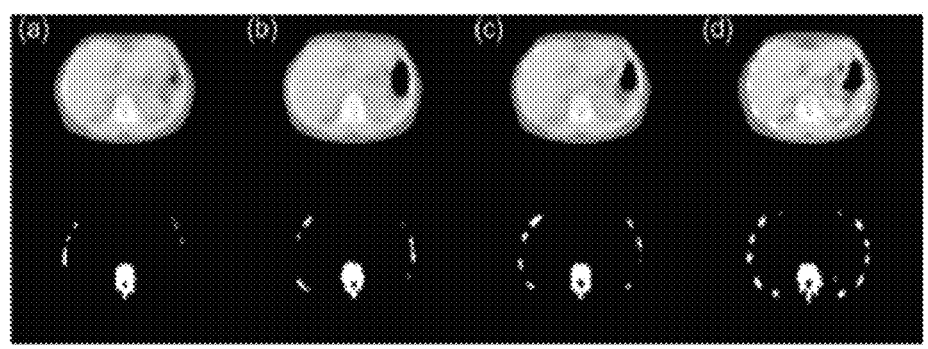

FIGS. 16 and 17 are exemplary diagrams of comparing images generated through input image of deep learning algorithms according to an exemplary embodiment of the present invention.

FIGS. 16 and 17 compare CT images and generated final attenuated images based on the PET scan image taken from the head to the upper body.

FIGS. 16 and 17, (a) is a final attenuation image derived using only the NAC image as an input image $\mu$-CNN$_{(NAC)}$, and (b) is a final attenuation derived from the first attenuation image and the first emission image as an input image. The image $\mu$-CNN$_{(MLAA)}$ is shown. And (c) shows the final attenuation image $\mu$-CNN$_{(MLAA+NAC)}$ derived from the NAC image, the first attenuation image, and the first emission image according to another embodiment of the present invention as input images, and (d) is Shows the $\mu$-CT image.

$\mu$-CNN$_{(NAC)}$ images showed some blocky and discontinuity artifacts in lung and upper liver, whereas $\mu$-CNN $_{(MLAA)}$ images achieved better bone and air cavity delineation and showed better contrast at some fat and water boundaries than $\mu$-CNN$_{(NAC)}$ images.

Meanwhile, $\mu$-CNN $_{(MLAA+NAC)}$ shows most similar to CT images in the bone contours of the shoulder, ribs and spine, and it can be seen that the moisture and fat contrast are the best As shown in Table 3 the similarity of the CNN-derived $\mu$-maps derived by the three methods relative to the $\mu$-CT is measured using the peak signal-to-noise ratio (PSNR), and structural similarity index (SSIM).

And the activity error relative to the $\lambda$-CT is calculated using the normalized root mean square error (NRMSE).

TABLE 3

| | | CNN$_{NAC}$ | CNN$_{MLAA}$ | CNN$_{MLAA+NAC}$ |
|---|---|---|---|---|
| $\mu$ | PSNR | 26.51 | 30.00 | 30.61 |
| | SSIM | 0.752 | 0.790 | 0.794 |
| $\lambda$ | NRMSE | 0.0031 | 0.0026 | 0.0025 |

Referring to Table 3, comparing the similarity of the $\mu$-map with the error of the $\lambda$-map, it can be seen that the case of using only MLAA (CNN$_{MLAA}$) has less error than the case of using only NAC (CNN$_{NAC}$). And it can be seen that among the three methods, when MLAA and NAC are used together (CNN$_{MLAA+NAC}$), the error is the least.

As described above, according to the present invention, it is possible to provide a high-quality attenuation image by solving a quantitative error due to noise and crosstalk artifacts of an image, which occur due to the simultaneous reconstruction technique without an additional scanning process of a medical device such as a separate CT or MRI.

A program for executing a method according to an exemplary embodiment of the present invention may be recorded in a computer readable recording medium.

The computer readable medium may include singly a program command, a data file, or a data structure or a combination thereof. The medium may be specially designed and configured for the present invention, or may be publicly known to and used by those skilled in the computer software field. Examples of the computer-readable recording medium include magnetic media such as a hard disk, a floppy disk, and a magnetic tape, optical media such as a CD-ROM and a DVD, magneto-optical media such as a floptical disk, and a hardware device which is specifically configured to store and execute the program command such as a ROM, a RAM, and a flash memory. Here, the medium may be a transmission medium such as an optical or metal line, a wave guide, or the like, including a carrier wave for transmitting a signal designating a program command, a data structure, and the like. Examples of the program command include a high-level language code executable by a computer by using an interpreter, and the like, as well as a machine language code created by a compiler.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims.

DESCRIPTION OF SYMBOLS

100: Positron emission tomography device
200: Positron emission tomography system
210: Collection unit
220: Generation unit 230: Control unit
240: Learning unit
241: Image generation unit
242: Error calculation unit
243: Weight adjustment unit
300: User terminal

What is claimed is:

1. A positron emission tomography system comprising:
a collection unit collecting a positron emission tomography sinogram (PET sinogram);
a generation unit applying a maximum likelihood reconstruction of attenuation and activity (MLAA) with time-of-flight (TOF) to the positron emission tomography sinogram and generating a first emission image and a first attenuation image, and a nonattenuation-corrected (NAC) image reconstructed without attenuation correction;
a control unit selecting at least one of the first emission image and the first attenuation image and the NAC image generated by the generation unit as an input image and generating and providing a final attenuation image by applying the learned deep learning algorithm to the input image; and
a learning unit collecting an attenuation image obtained through additional scanning based on the positron emission tomography sinogram and making a deep learning algorithm be learned by using at least one of the first emission image, the first attenuation image and the NAC image generated from the positron emission tomography sinogram and the obtained attenuation image, wherein:
the learning unit includes,
an image generation unit generating a second attenuation image from the first attenuation image through the deep learning algorithm,
an error calculation unit calculating an error between the second attenuation image and the obtained attenuation image, and
a weight adjustment unit performing repeated learning by readjusting weights of a plurality of filters included in the deep learning algorithm so as to generate a final attenuation image in which the error value becomes a value equal to or less than a threshold value.

2. The positron emission tomography system of claim 1, wherein:
the image generation unit
generates a plurality of feature maps from the input image by using the filter of the deep learning algorithm and generates a sample downsized from the generated feature map at a predetermined ratio, and repeats a process of generating the plurality of feature maps in the downsized sample by using the filter until a size of the sample reaches a predetermined reference size, and
upsizes the sample at a predetermined ratio when the size of the sample reaches the predetermined reference size and generates the second attenuation image when the size of the upsized sample coincides with an initial size by repeating a process of generating the plurality of feature maps in the upsized sample by using the filter.

3. The positron emission tomography system of claim 2, wherein:
the image generation unit
upsizes the sample and collects feature maps having the same size as the upsized sample and combines the collected feature maps and the sample at the time of generating the plurality of feature maps and generates the plurality of feature maps from the combined sample.

4. The positron emission tomography system of claim 1, wherein:
the control unit,
selects the first attenuation, the first emission image and the NAC image as the input image to generate a final attenuation image through the learned deep learning algorithm.

5. The positron emission tomography system of claim 4, wherein:
the control unit,
selects some voxel data groups from the first attenuation image, the first emission image and the NAC image and applies the learned deep learning algorithm to the entire first attenuation image, first emission image and the NAC image by repeating a process of applying the learned deep learning algorithm to the selected voxel data groups to generate the final attenuation image in a 3D type.

6. The positron emission tomography system of claim 1, wherein:
the control unit,
generates and provides a final emission image obtained by correcting the final attenuation image by using the first emission image and the final attenuation image.

7. A method for reconstructing an image in a positron emission tomography system, the method comprising:
collecting a positron emission tomography sinogram (PET sinogram);
applying an maximum likelihood reconstruction of attenuation and activity (MLAA) with time-of-flight (TOF) to the positron emission tomography sinogram and generating a first emission image and a first attenuation image, and a nonattenuation-corrected (NAC) image reconstructed without attenuation correction;
selecting the generated first attenuation image, the first attenuation image and NAC image as an input image;
generating and providing a final attenuation image by applying the learned deep learning algorithm to the input image;
generating and providing a final emission image corrected by using the first emission image and the final attenuation image; and
collecting an attenuation image obtained through additional scanning, which corresponds to the positron emission tomography image and learning a deep learning algorithm by using the input image and the obtained attenuation image, wherein:
the learning of the deep learning algorithm includes
generating a second attenuation image from the first attenuation image through the deep learning algorithm,
calculating an error between the second attenuation image and the obtained attenuation image, and
performing repeated learning by readjusting weights of a plurality of filters included in the deep learning algorithm so as to generate a final attenuation image in which the error value becomes a value equal to or less than a threshold value.

8. The method of claim 7, wherein:
the generating of the second attenuation image includes
generating a plurality of feature maps from the input image by using a filter of the deep learning algorithm, generating a sample downsized from the generated feature map at a predetermined ratio and generating the plurality of feature maps by using the filter in the downsized sample, upsizing the sample at a predetermined ratio and collecting a downsized feature map having the same size as the upsized sample when the sample reaches a predetermined reference size, generating the plurality of feature maps by using the filter in the upsized sample and the collected feature map, and generating a second attenuation image when a size of the upsized sample coincides with an initial size.

9. The method of claim 7, wherein:

when some voxel data groups are selected in the first attenuation image or the first emission image or NAC image as the input image, in the generating and providing of the final attenuation image, the final attenuation image is generated in a 3D type by applying the learned deep learning algorithm to the selected voxel data groups.

10. A method for reconstructing an image in a positron emission tomography system, the method comprising:

collecting a first emission image and a first attenuation image generated by an maximum likelihood reconstruction of attenuation and activity (MLAA) with time-of-flight (TOF) with a positron emission tomography sinogram (PET sinogram), and a nonattenuation-corrected (NAC) image reconstructed without attenuation correction;

selecting at least one of the generated first attenuation image, the first attenuation image and NAC image as an input image;

generating and providing a final attenuation image by applying the learned deep learning algorithm to the input image;

generating and providing a final emission image corrected by using the first emission image and the final attenuation image; and collecting an attenuation image obtained through additional scanning, which corresponds to the positron emission tomography image and learning a deep learning algorithm by using the input image and the obtained attenuation image, wherein:

the learning of the deep learning algorithm includes generating a second attenuation image from the first attenuation image through the deep learning algorithm, calculating an error between the second attenuation image and the obtained attenuation image, and performing repeated learning by readjusting weights of a plurality of filters included in the deep learning algorithm so as to generate a final attenuation image in which the error value becomes a value equal to or less than a threshold value.

11. The method of claim 10, wherein:

the generating of the second attenuation image includes generating a plurality of feature maps from the input image by using a filter of the deep learning algorithm, generating a sample downsized from the generated feature map at a predetermined ratio and generating the plurality of feature maps by using the filter in the downsized sample, upsizing the sample at a predetermined ratio and collecting a downsized feature map having the same size as the upsized sample when the sample reaches a predetermined reference size, generating the plurality of feature maps by using the filter in the upsized sample and the collected feature map, and generating a second attenuation image when a size of the upsized sample coincides with an initial size.

12. The method of claim 10, wherein:

when the first attenuation image, the first emission image and NAC image are selected as the input image, in the generating and providing of the final attenuation image, the final attenuation image is generated by applying the learned deep learning algorithm to the first attenuation image and the first emission image.

13. The method of claim 10, wherein:

when some voxel data groups are selected in the first attenuation image or the first emission image or NAC image as the input image, in the generating and providing of the final attenuation image, the final attenuation image is generated in a 3D type by applying the learned deep learning algorithm to the selected voxel data groups.

* * * * *